(12) United States Patent
Sakaguchi et al.

(10) Patent No.: US 10,016,175 B2
(45) Date of Patent: Jul. 10, 2018

(54) X-RAY DIAGNOSTIC APPARATUS AND IMAGE PROCESSING APPARATUS

(71) Applicant: Toshiba Medical Systems Corporation, Otawara-shi (JP)

(72) Inventors: Takuya Sakaguchi, Utsunomiya (JP); Hisato Takemoto, Amherst, MA (US); Yuichiro Watanabe, Yaita (JP); Ryuji Zaiki, Utsunomiya (JP); Ryoichi Nagae, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 311 days.

(21) Appl. No.: 14/672,875

(22) Filed: Mar. 30, 2015

(65) Prior Publication Data

US 2015/0289831 A1   Oct. 15, 2015

(30) Foreign Application Priority Data

Apr. 10, 2014   (JP) ................. 2014-081311

(51) Int. Cl.
*A61B 5/05* (2006.01)
*A61B 6/00* (2006.01)
*G06T 7/00* (2017.01)

(52) U.S. Cl.
CPC ............ *A61B 6/5205* (2013.01); *A61B 6/481* (2013.01); *G06T 7/0016* (2013.01); *A61B 6/4441* (2013.01);
(Continued)

(58) Field of Classification Search
CPC ....... A61B 6/5205; A61B 6/481; A61B 6/469; A61B 6/4464; A61B 6/504; A61B 6/5217;
(Continued)

(56) References Cited

U.S. PATENT DOCUMENTS 6,176,838 B1 *   1/2001   Sase ................. A61B 6/481
                                              600/431
7,496,175 B2 *   2/2009   Sakaguchi ........... A61B 6/4233
                                              378/95
(Continued)

FOREIGN PATENT DOCUMENTS

JP   2008-136800   6/2008

OTHER PUBLICATIONS

J. H. Bürsch, et al., "Parametric Imaging", Symposium on Digital Radiography, vol. 23, No. 2, Jun. 1985, pp. 321-333.
(Continued)

*Primary Examiner* — Sanjay Cattungal
(74) *Attorney, Agent, or Firm* — Oblon, McClelland, Maier & Neustadt, L.L.P.

(57) ABSTRACT

An X-ray diagnostic apparatus in embodiments includes a calculating module, a generator, and a changing module. The calculating module calculates feature quantity concerning a flow of a contrast material for each pixel in a predetermined section based on temporal transition in signal intensity of the contrast material in a predetermined section of a plurality of X-ray images radiographed with time by using the contrast material. The generator generates a first color image in which color information corresponding to the feature quantity concerning the flow of the contrast material in a first section as the predetermined section is reflected in each pixel. The changing module changes the predetermined section to a second section that is within the first section. the generator generates a second color image in which color information corresponding to the feature quantity concerning the flow of the contrast material in the second section is reflected in each pixel based on the color information corresponding to the second section out of the color information corresponding to the feature quantity concerning the
(Continued)

flow of the contrast material in the first section and the feature quantity calculated in the second section.

20 Claims, 24 Drawing Sheets

(52) U.S. Cl.
CPC ............. *A61B 6/4464* (2013.01); *A61B 6/469* (2013.01); *A61B 6/501* (2013.01); *A61B 6/504* (2013.01); *A61B 6/5217* (2013.01); *G06T 2207/10116* (2013.01); *G06T 2207/30104* (2013.01)

(58) Field of Classification Search
CPC ..... A61B 6/501; A61B 6/4441; G06T 7/0016; G06T 2207/10116; G06T 2207/30104
USPC ................................................ 600/407–430
See application file for complete search history.

(56) References Cited

U.S. PATENT DOCUMENTS

| | | |
|---|---|---|
| 8,150,125 B2 | 4/2012 | Baumgart et al. |
| 2011/0235885 A1* | 9/2011 | Rauch .................. A61B 6/4441 382/131 |
| 2015/0071520 A1 | 3/2015 | Takemoto et al. |

OTHER PUBLICATIONS

Robert A. Vogel, "The radiographic assessment of coronary blood flow parameters", Perspective, vol. 72, No. 3, Sep. 1985, pp. 460-465.

\* cited by examiner

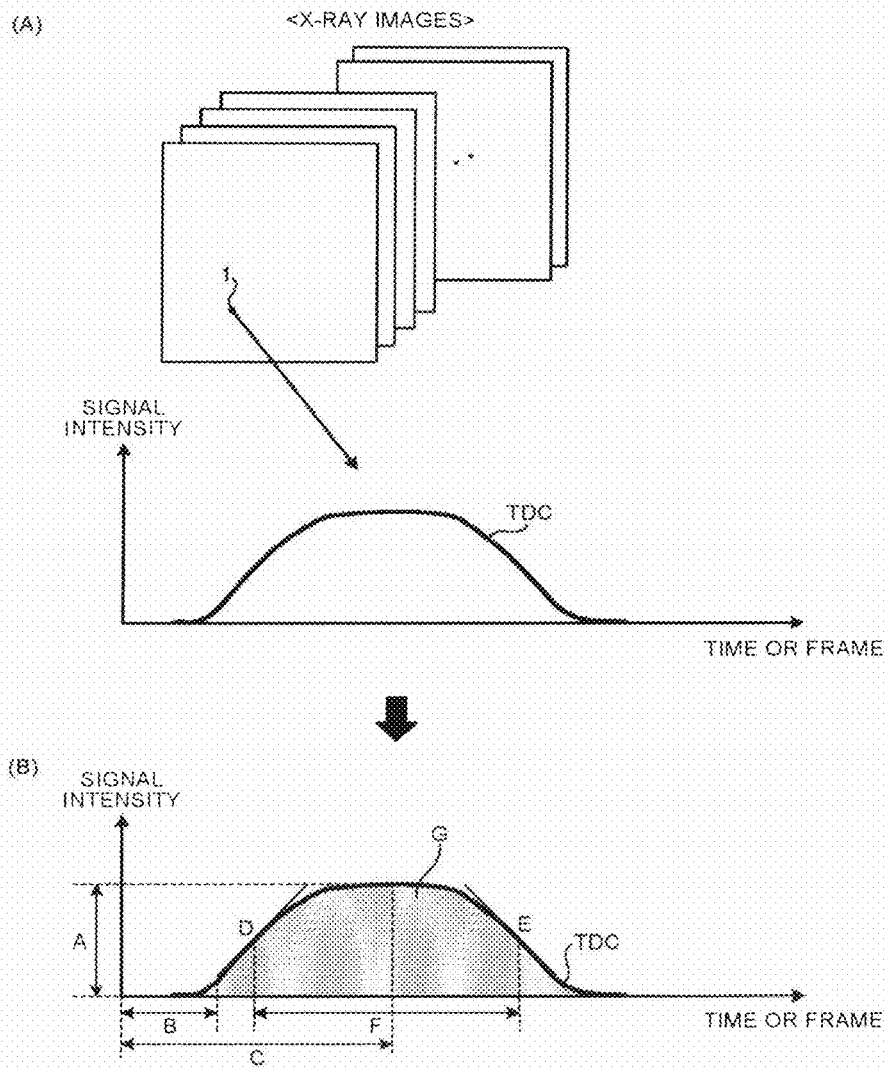

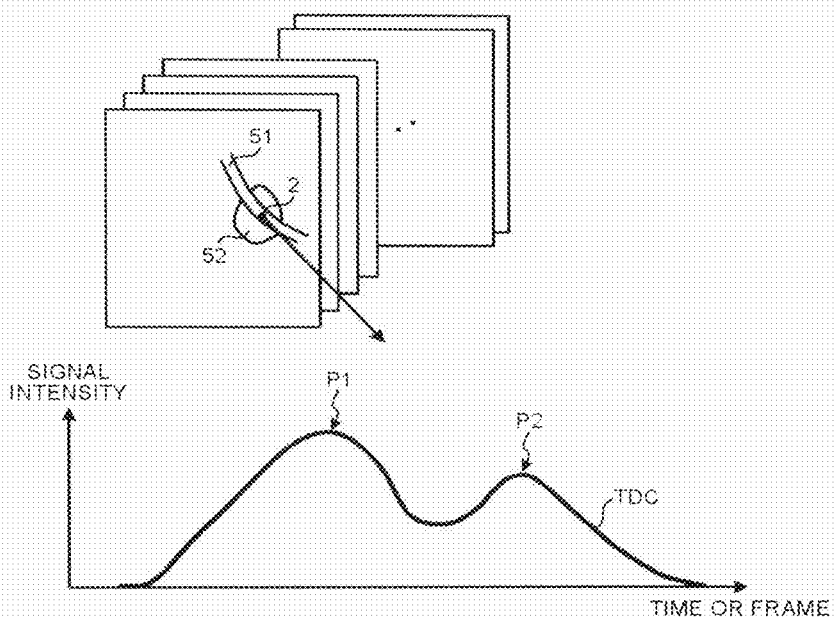
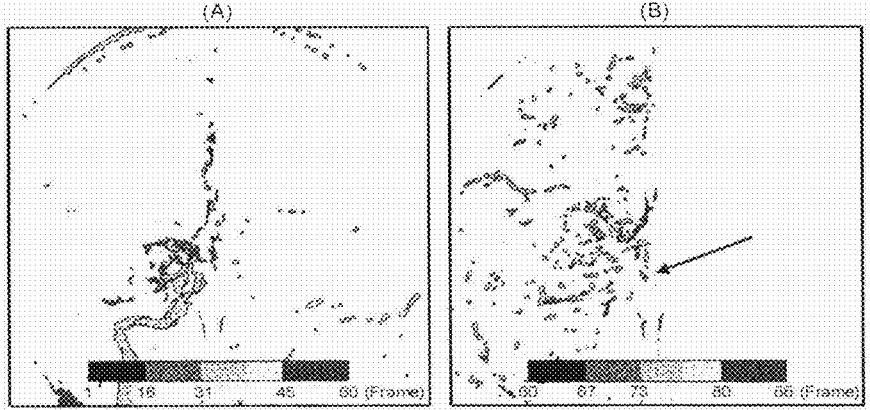

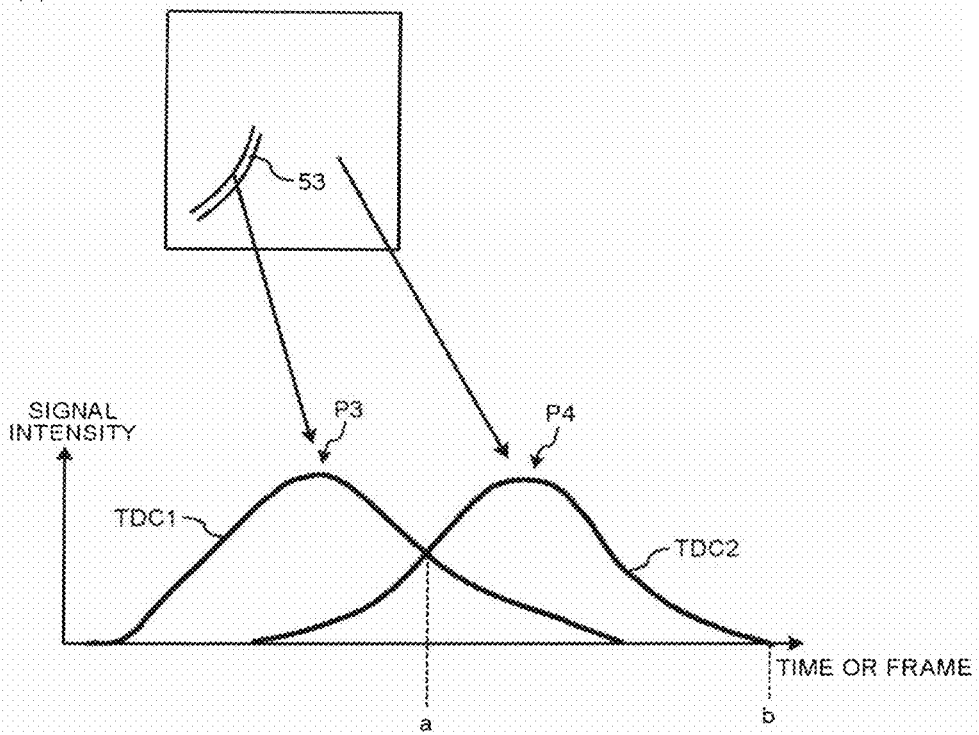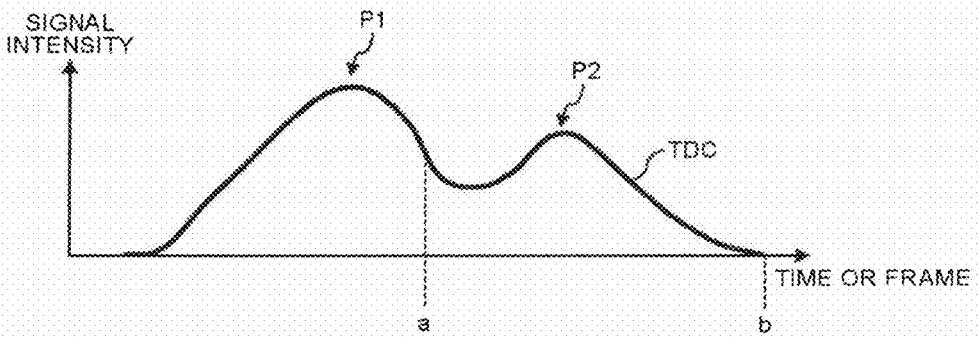
FIG.5

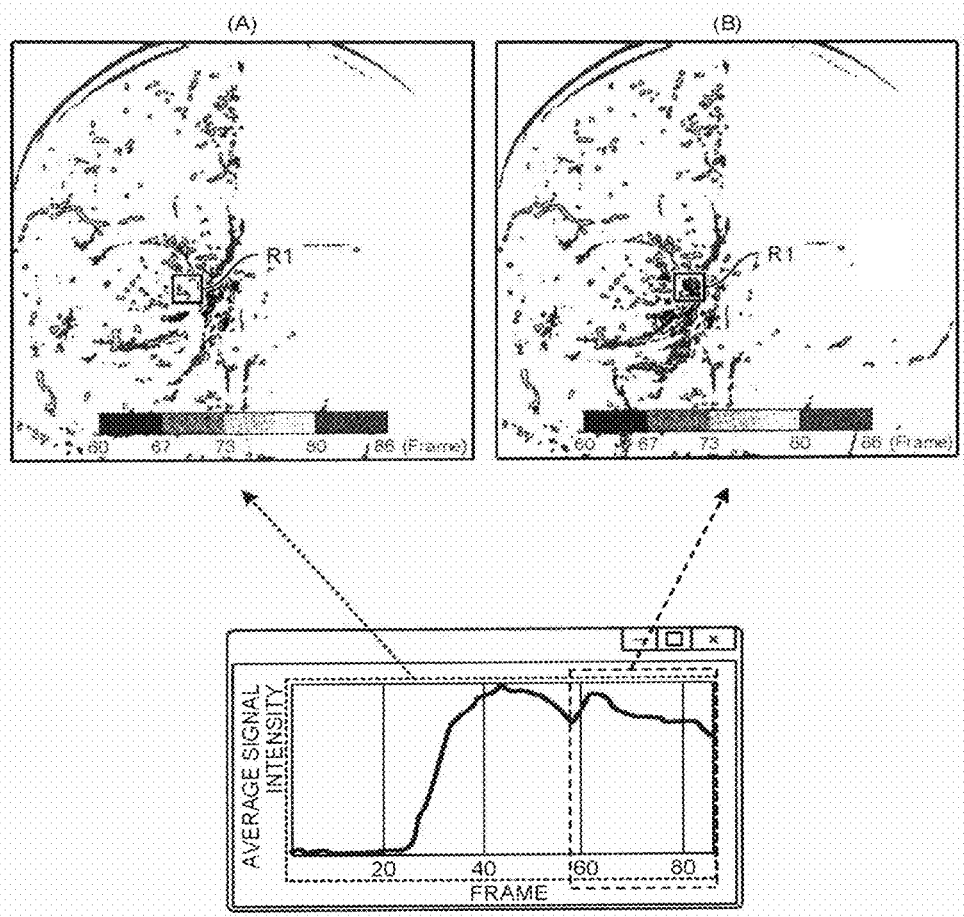

FIG.8A
(A)
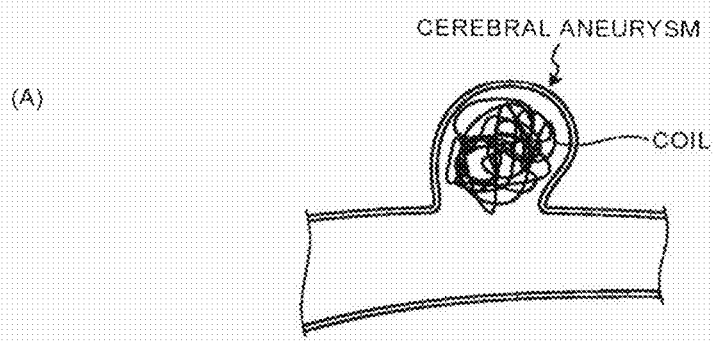
(B)
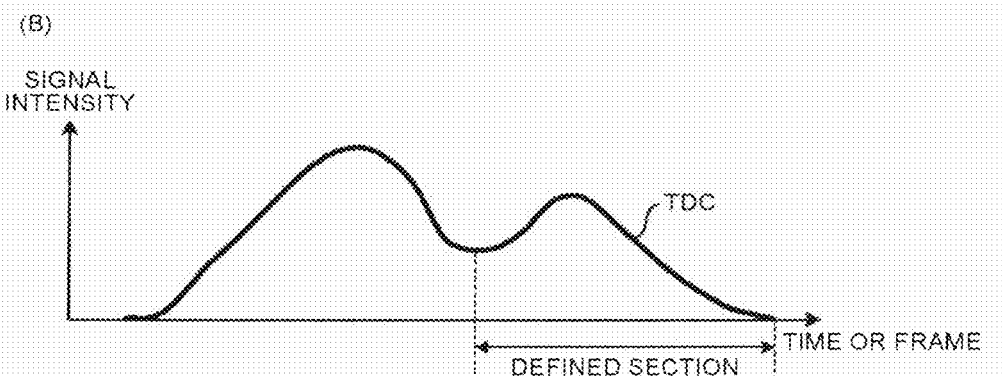

FIG.8B
(A)
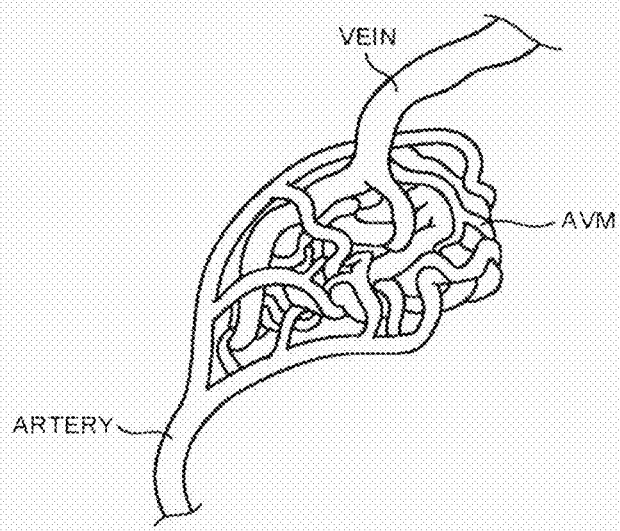
(B)
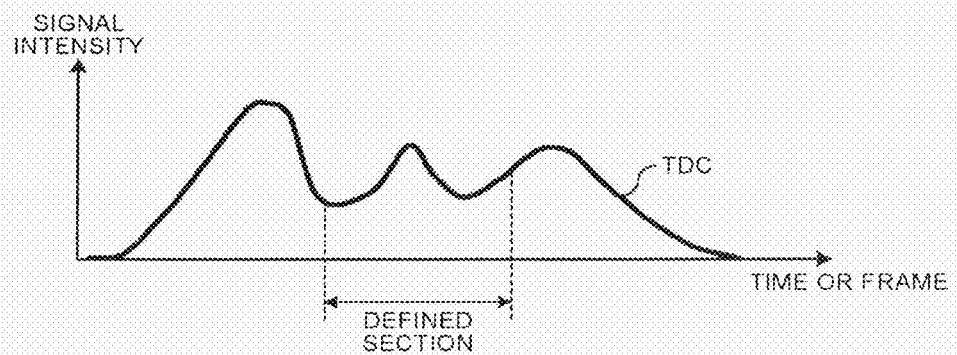

FIG.8C
(A)
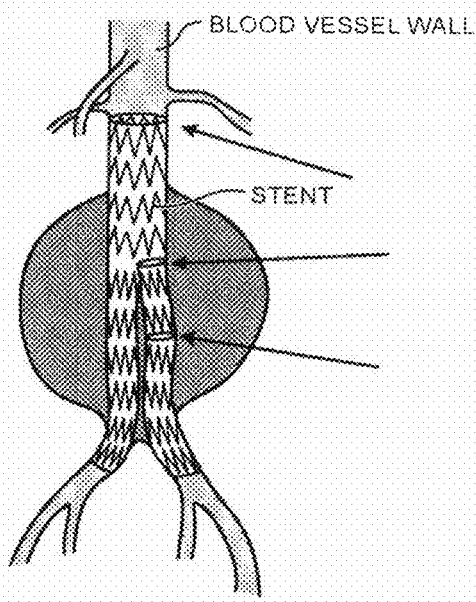
(B)
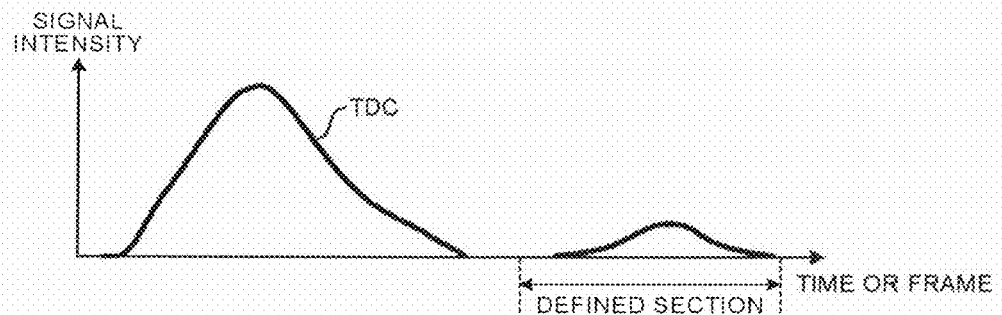

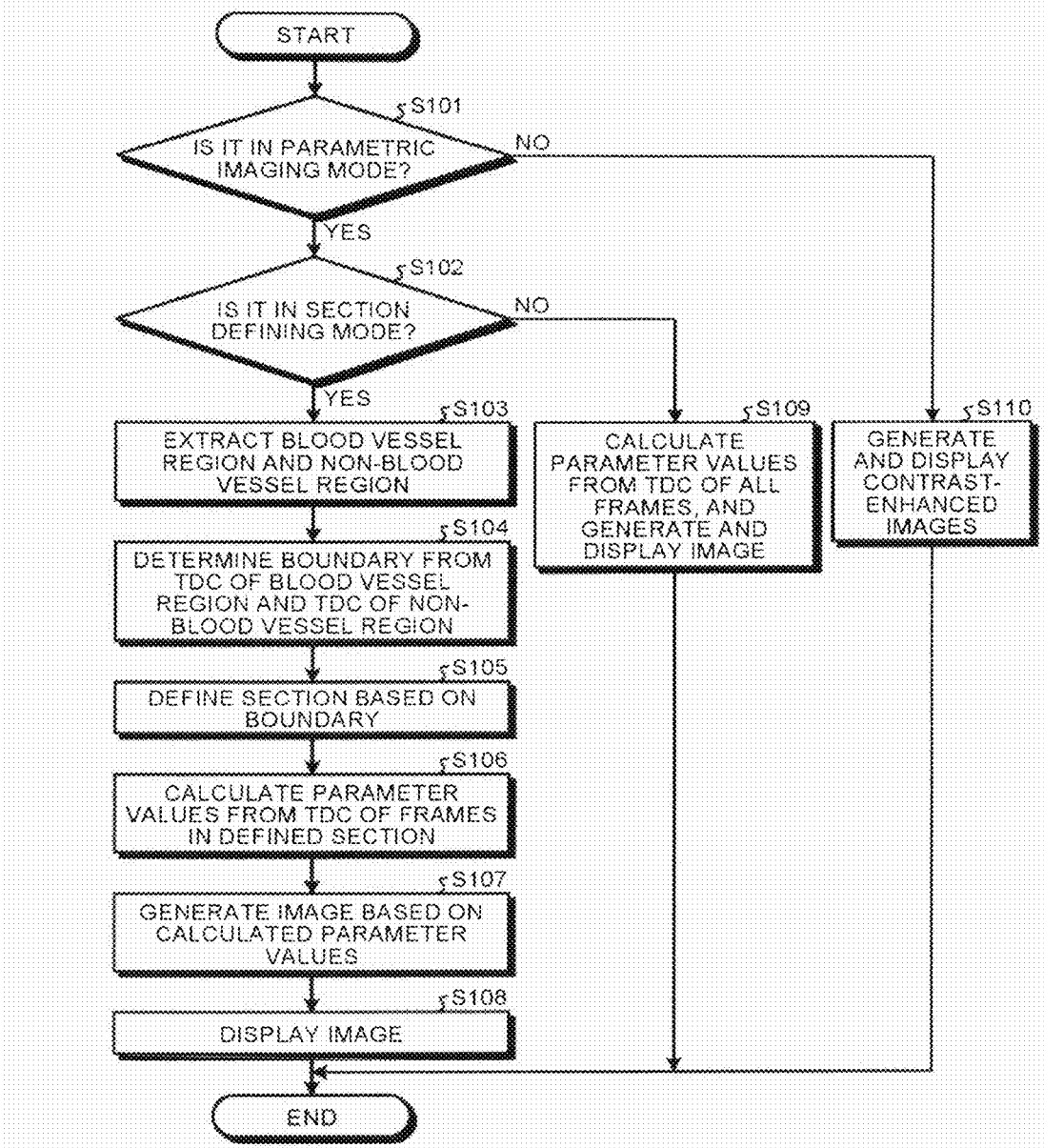

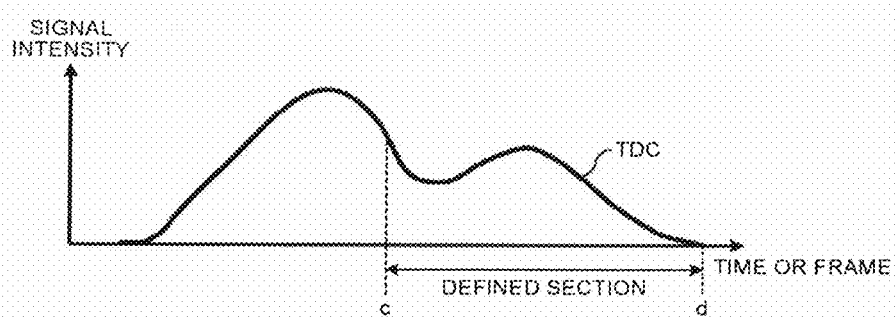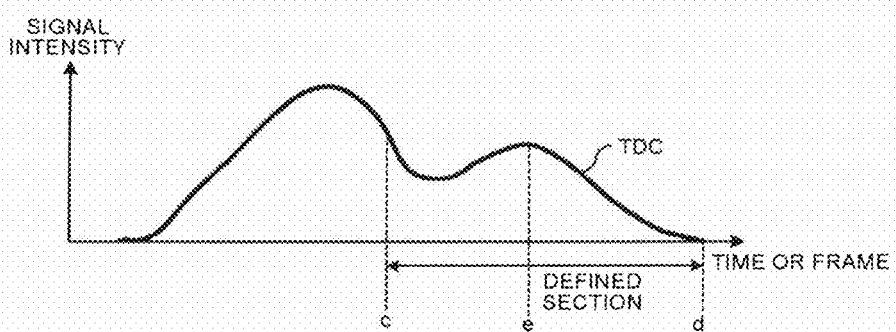
FIG.12

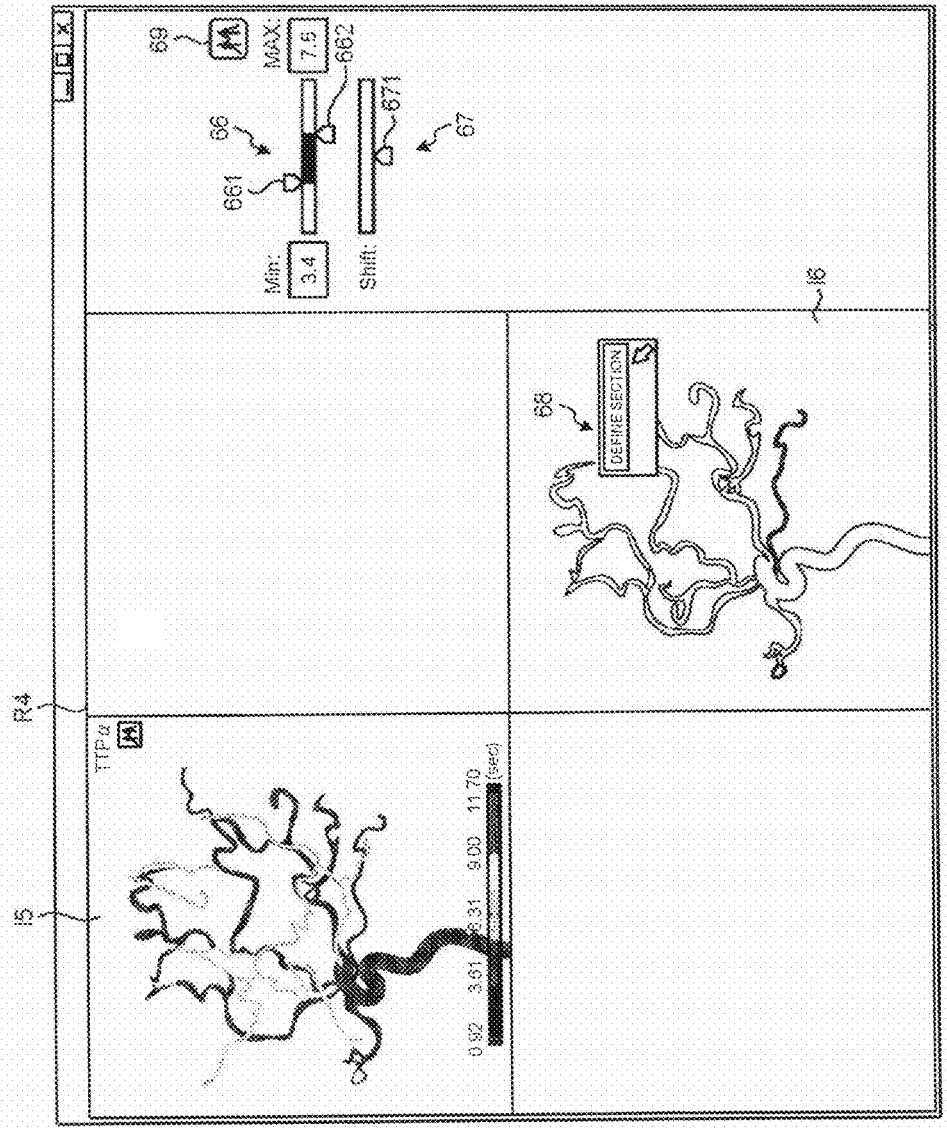

FIG.15B
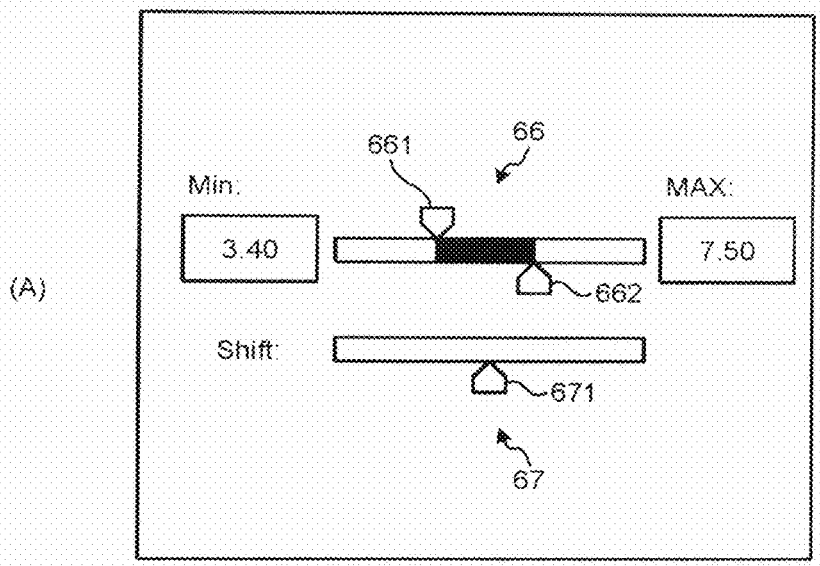
(A)
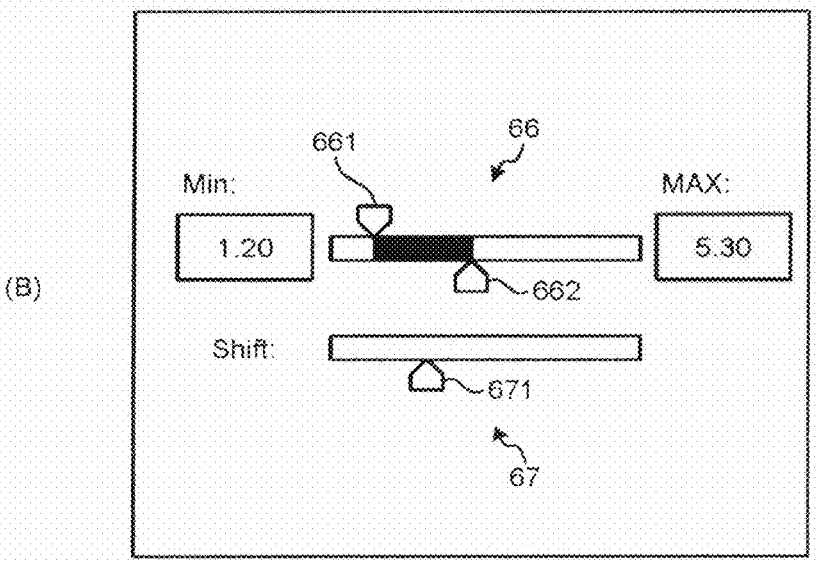
(B)

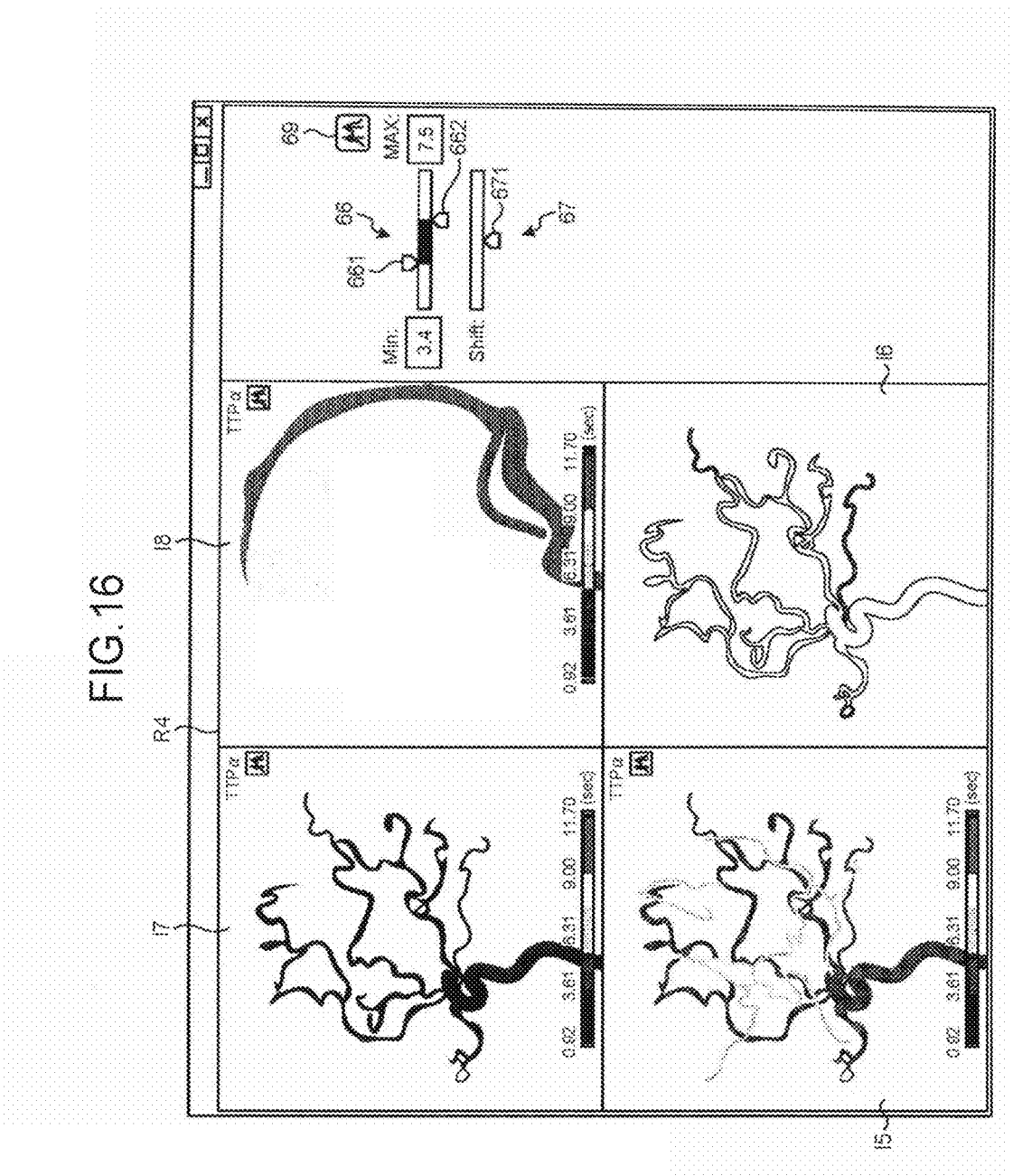

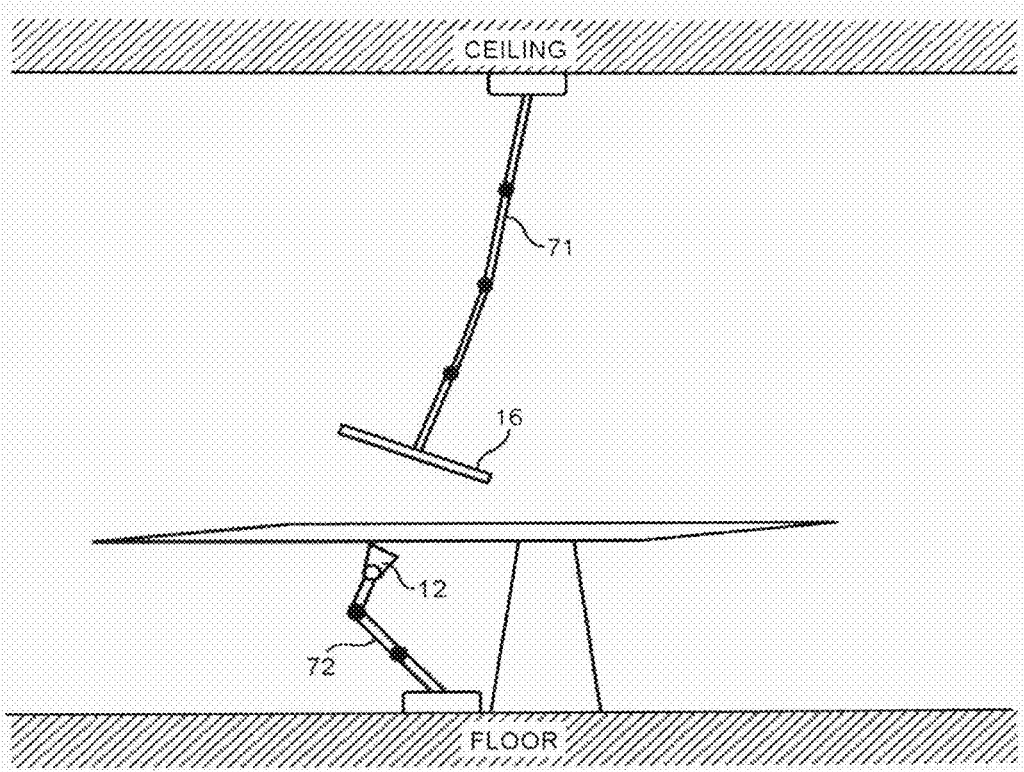

X-RAY DIAGNOSTIC APPARATUS AND IMAGE PROCESSING APPARATUS

CROSS-REFERENCE TO RELATED APPLICATIONS

This application is based upon and claims the benefit of priority from Japanese Patent Application No. 2014-081311, filed on Apr. 10, 2014, the entire contents of all of which are incorporated herein by reference.

FIELD

Embodiments described herein relate generally to an X-ray diagnostic apparatus and an image processing apparatus.

BACKGROUND

In X-ray diagnostic apparatuses, conventionally known is an image rendering method that renders blood flow information, which is collected by injecting a contrast material, by predetermined parameter values. Hereinafter, such an image rendering method is described as parametric imaging. In the above-described parametric imaging, a time density curve (TDC) of the contrast material is calculated for each pixel, and by using the calculated TDC, various parameter values are calculated. As for the parameter values in the parametric imaging, calculated are the time it takes to reach a peak in the TDC (time to peak (TTP)), the height of the peak (peak height (PH)), the area of the TDC (area under curve (AUC)), the arrival time of the contrast material (arrival time (AT)), the time it takes to wash out the contrast material from the peak (Wash-out), and a mean transit time (MTT), for example.

In the parametric imaging, the parameter values corresponding to the blood flow information desired by an observer are calculated for each pixel, and an image in which the respective pixels in the image are colorized by colors corresponding to the calculated parameter values is generated and displayed. This enables the observer to perform various diagnoses based on the blood flow information rendered by the displayed image. In the above-described conventional technology, however, there have been some limitations in rendering the image by the parametric imaging.

BRIEF DESCRIPTION OF THE DRAWINGS

FIG. 2A is a diagram for explaining an example of parametric imaging in the first embodiment;

FIG. 3A is a diagram for explaining a problem according to a conventional technology;

FIG. 3B is a diagram for explaining the problem in the conventional technology;

FIG. 5 is a diagram for explaining one example of extracting a section by a calculating module in the first embodiment;

FIG. 7 is a diagram illustrating one example of the parametric imaging in the first embodiment;

FIG. 8A is a diagram for explaining an application example of the X-ray diagnostic apparatus in the first embodiment;

FIG. 8B is a diagram for explaining an application example of the X-ray diagnostic apparatus in the first embodiment;

FIG. 8C is a diagram for explaining an application example of the X-ray diagnostic apparatus in the first embodiment;

FIG. 9 is a flowchart illustrating a procedure of processing performed by the X-ray diagnostic apparatus in the first embodiment;

FIG. 12 is a diagram for explaining one example of processing performed by an X-ray diagnostic apparatus in the third embodiment;

FIG. 15A is a diagram illustrating an example of a GUI that receives an operation of designating a second section in the third embodiment;

FIG. 15B is a diagram illustrating an example of the GUI that receives the operation of designating the second section in the third embodiment;

FIG. 16 is a diagram illustrating a display example of a plurality of color images in the third embodiment; and FIG. 17 is a diagram illustrating one example of the X-ray diagnostic apparatus in the third embodiment.

DETAILED DESCRIPTION

According to an embodiment, an X-ray diagnostic apparatus includes a calculating module, a generator, and a changing module. The calculating module calculates feature quantity concerning a flow of a contrast material for each pixel in a predetermined section based on temporal transition in signal intensity of the contrast material in a predetermined section of a plurality of X-ray images radiographed with time by using the contrast material. The generator generates a first color image in which color information corresponding to the feature quantity concerning the flow of the contrast material in a first section as the predetermined section is reflected in each pixel. The changing module changes the predetermined section to a second section that is within the first section. the generator generates a second color image in which color information corresponding to the feature quantity concerning the flow of the contrast material in the second section is reflected in each pixel based on the color information corresponding to the second section out of the color information corresponding to the feature quantity concerning the flow of the contrast material in the first section and the feature quantity calculated in the second section.

With reference to the accompanying drawings, the following describes in detail exemplary embodiments of an X-ray diagnostic apparatus and an image processing apparatus according to the present application. The X-ray diagnostic apparatus and the image processing apparatus in the application, however, are not intended to be limited by the following embodiments.

First Embodiment

Figure 1:
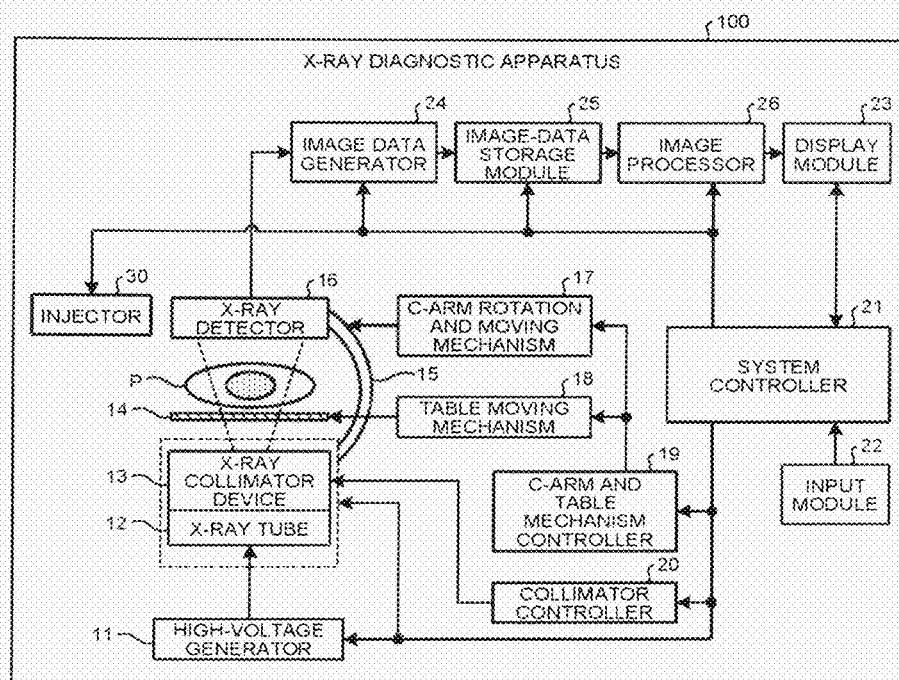
FIG. 1 is a block diagram illustrating one example of the configuration of an X-ray diagnostic apparatus according to a first embodiment.

FIG. 1 is a block diagram illustrating one example of the configuration of an X-ray diagnostic apparatus 100 according to a first embodiment. As illustrated in FIG. 1, the X-ray diagnostic apparatus 100 in the first embodiment includes a high-voltage generator 11, an X-ray tube 12, an X-ray diaphragm, device 13, a couchtop 14, a C-arm 15, and an X-ray detector 16. The X-ray diagnostic apparatus 100 in the first embodiment further includes a C-arm rotation and moving mechanism 17, a couchtop moving mechanism 18, a C-arm and couchtop mechanism controller 19, a diaphragm controller 20, a system controller 21, an input module 22, and a display module 23. The X-ray diagnostic apparatus 100 in the first embodiment further includes an image data generator 24, an image-data storage module 25, and an image processor 26. The X-ray diagnostic apparatus 100 is coupled to an injector 30.

The injector 30 is a device to inject a contrast material through a catheter inserted to a subject P. The start of injecting the contrast material from the injector 30 may be performed in accordance with an injection-start instruction received via the system controller 21 which will be described later, or may be performed in accordance with an injection-start instruction input directly to the injector 30 by an operator.

The high-voltage generator 11, under the control of the system controller 21, generates a high voltage and supplies the generated high voltage to the X-ray tube 12. The X-ray tube 12, by using the high voltage supplied from the high-voltage generator 11, generates an X-ray.

The X-ray diaphragm device 13, under the control of the diaphragm controller 20, narrows the X-ray generated by the X-ray tube 12 such that the region of interest of the subject P is selectively irradiated with the X-ray. For example, the X-ray diaphragm device 13 has four slidable diaphragm blades. The X-ray diaphragm device 13, under the control of the diaphragm controller 20, makes the diaphragm blades slide to narrow the X-ray generated by the X-ray tube 12 and to irradiate the subject P. The couchtop 14 is a bed on which the subject P is placed, and is arranged on a couch not depicted. Note that the subject P is not included in the X-ray diagnostic apparatus 100.

The X-ray detector 16 detects the X-ray transmitted through the subject P. For example, the X-ray detector 16 has detection elements arrayed in a matrix. Each of the detection elements transforms and accumulates the X-ray transmitted through the subject P into an electrical signal, and transmits the accumulated electrical signal to the image data generator 24.

The C-arm 15 holds the X-ray tube 12, the X-ray diaphragm device 13, and the X-ray detector 16. The X-ray tube 12 and the X-ray diaphragm device 13 are arranged by the C-arm 15 so as to face the X-ray detector 16 with the subject P interposed.

The C-arm rotation and moving mechanism 17 is a mechanism to rotate and move the C-arm 15, and the couchtop moving mechanism 18 is a mechanism to move the couchtop 14. The C-arm and couchtop mechanism controller 19, under the control of the system controller 21, adjusts the rotation and moving of the C-arm 15 and the moving of the couchtop 14 by controlling the C-arm rotation and moving mechanism 17 and the couchtop moving mechanism 18, respectively. The diaphragm controller 20, under the control of the system controller 21, controls the irradiation range of the X-ray with which the subject P is irradiated, by adjusting the opening of the diaphragm blades of the X-ray diaphragm device 13.

The image data generator 24 generates image data by using an electrical signal transformed from the X-ray by the X-ray detector 16, and stores the generated image data in the image-data storage module 25. For example, the image data generator 24 performs current-voltage conversion, analog to digital (A/D) conversion, and parallel-serial conversion on the electrical signal received from the X-ray detector 16, and generates image data.

The image-data storage module 25 stores therein the image data generated by the image data generator 24. For example, the image-data storage module 25 stores therein the image data in which a predetermined region of the subject P to which a contrast material has been injected was radiographed in time series. The image-data storage module 25 further stores therein color images generated by the image processor 26. The color images will be described later in detail.

The image processor 26 performs a variety of image processing on the image data stored in the image-data storage module 25. The image processing performed by the image processor 26 will be described later in detail.

The input module 22 receives various instructions from the operator such as a doctor and an engineer who operates the X-ray diagnostic apparatus 100. The input module 22 has a mouse, a keyboard, a button, a trackball, and a joystick, for example. The input module 22 transfers the instructions received from the operator to the system controller 21.

The display module 23 displays a graphical user interface (GUI) to receive the instructions of the operator, and the image data stored in the image-data storage module 25, for example. The display module 23 has a monitor, for example. The display module 23 may have a plurality of monitors.

The system controller 21 controls the overall operation of the X-ray diagnostic apparatus 100. For example, the system controller 21 controls the high-voltage generator 11 in accordance with the instructions of the operator transferred from the input module 22 to adjust the voltage supplied to the X-ray tube 12, so as to control the X-ray dosage with which the subject P is irradiated and the turning on and off the X-ray. Furthermore, the system controller 21 controls the C-arm and couchtop mechanism controller 19 in accordance with the instructions of the operator, to adjust the rotation and moving of the C-arm 15 and the moving of the couchtop 14, for example. The system controller 21 further controls the diaphragm controller 20 in accordance with the instructions of the operator so as to control the irradiation range of the X-ray with which the subject P is irradiated by adjusting the opening of the diaphragm blades of the X-ray diaphragm device 13, for example.

Moreover, the system controller 21 controls, in accordance with the instructions of the operator, image-data generation processing performed by the image data generator 24, and image processing, analyzing processing, or others performed by the image processor 26. The system controller 21 further has control of displaying the GUI to receive the instructions of the operator, the images stored in the image-data storage module 25, and others, on the monitor of the display module 23. The system controller 21 controls the timing of injecting the contrast material, by transmitting signals of the start and end of contrast material injection to the injector 30.

In the foregoing, one example of the overall configuration of the X-ray diagnostic apparatus 100 has been explained. The X-ray diagnostic apparatus 100 in the first embodiment thus configured makes it possible to improve the rendering of images by parametric imaging. Specifically, by calculating parameter values from the transition in signal intensity of the contrast material in frames in a predetermined section out of a plurality of X-ray images collected with time and generating color images based on the calculated parameter values, the X-ray diagnostic apparatus 100 improves the rendering of images by the parametric imaging by the processing performed by the image processor 26 which will be described in detail in the following.

Figure 2B:
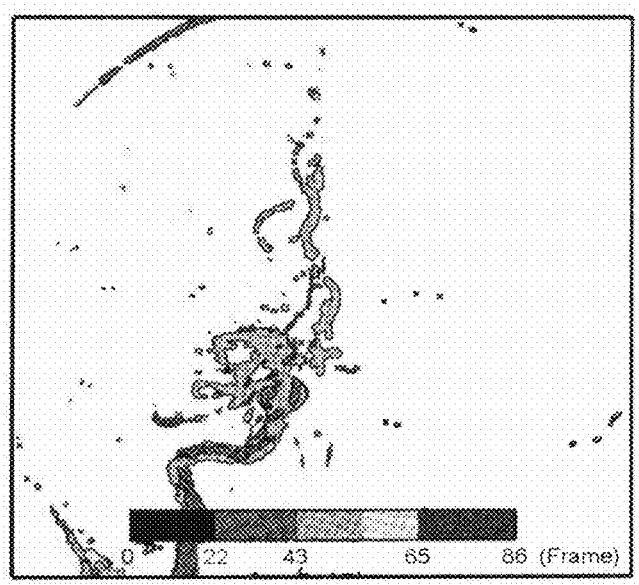
FIG. 2B is a diagram for explaining the example of the parametric imaging in the first embodiment.

First, the parametric imaging will be described with reference to FIGS. 2A and 2B. FIGS. 2A and 2B are diagrams for explaining an example of the parametric imaging in the first embodiment. FIG. 2A illustrates examples of parameters in the parametric imaging, and FIG. 2B illustrates an example of a color image by the parametric imaging.

As in the foregoing, the parametric imaging calculates a time density curve (TDC) of a contrast material for each pixel, and by using the calculated TDC, calculates various parameter values. As illustrated in FIG. 2A (A), in the parametric imaging, the TDC of each pixel in a plurality of X-ray images radiographed with time by using the contrast material (hereinafter, described as contrast-enhanced images) is calculated, for example. That is, in the parametric imaging, as illustrated in the TDC of a pixel 1 in FIG. 2A (A), with the radiographed time or frame of the contrast-enhanced images as the abscissa axis and with the signal intensity as the ordinate axis, the TDC is calculated for each pixel in the contrast-enhanced images. The contrast-enhanced image is a difference image (DSA image) in which background elements such as bones are removed by performing the subtraction (difference processing) of a mask image that was radiographed in a state of the contrast material not being injected from a contrast image that was radiographed in a state of the contrast material being injected.

In the parametric imaging, the parameter values for each pixel are then calculated based on the calculated TDC. For example, in the parametric imaging, as illustrated in FIG. 2A (B), calculated are "A: peak height (PH)" indicative of a maximum value of signal intensity, "B: arrival time (AT)" indicative of the time until starting to be stained by the contrast material, "C: time to peak (TTP)" indicative of the time until reaching the maximum value of signal intensity, "D: wash-in" indicative of the time until reaching the maximum value of signal intensity after starting to be stained by the contrast material, "E: wash-out" indicative of the time until washing out the contrast material after the time the maximum value of signal intensity is indicated, "F: width" indicative of a half value width of the maximum value of the TDC, and "G: area under curve (AUC)" indicative of the area of the TDC (the flowed amount of the contrast material for each pixel), for example.

In the parametric imaging, it is determined that the time or frame at which the signal intensity exceeds a predetermined percentage (for example, 5%) of the maximum value (PH) is the start of being stained, and the time or frame at which the signal intensity falls below a predetermined percentage (for example, 5%) of the maximum value (PH) is the time point at which the contrast material is washed out. The examples illustrated in FIG. 2AB are one example after all, and as for the parameters, calculated are, other than those illustrated, a slope indicative of the gradient of the TDC up to the maximum intensity and a mean transit time (MTT) indicative of the mean transit time of the contrast material, for example.

When the parameter values are calculated in this manner for each pixel in the contrast-enhanced images, in the parametric imaging, a color image in which the values of a predetermined parameter for each pixel are reflected is generated. For example, as illustrated in FIG. 2B, a color image concerning the parameter "TTP" is generated. In FIG. 2B, illustrated is a situation in which the contrast-enhanced images are composed of 86 frames. That is, color information is allocated to all the 86 frames included in the contrast-enhanced images to generate a color image in which a color corresponding to the frame at which the signal intensity reached a maximum value for each pixel is reflected. This enables the observer to check a state of blood flow at a glance from the color information in the color image.

As in the foregoing, in the parametric imaging, a color image is generated and displayed based on the TDC calculated for each pixel. In a conventional parametric imaging, however, there are some limitations in rendering the image, and there have been cases in which it is difficult to display a color image desired by the observer. FIGS. 3A and 3B are diagrams for explaining a problem in the conventional technology. For example, in the X-ray images, as illustrated in the upper portion of FIG. 3A, there are cases in which a blood vessel 51 and a tissue 52 overlap with each other in the depth direction. In contrast-enhanced images in such a state, as illustrated in the lower portion of FIG. 3A, the TDC of a pixel 2 in the region where the tissue 52 overlaps behind the blood vessel 51 includes two peaks (P1 and P2), for example. That is, the TDC illustrated in FIG. 3A is to include the peak P1 indicative of an increase in signal intensity by the flow of the contrast material into the blood vessel 51, and the peak P2 indicative of an increase in signal intensity by the flow of the contrast material into the tissue 52.

In the conventional parametric imaging, because each parameter is calculated with the TDC of the radiographed time or the total frames of the contrast-enhanced images as the target, in the case of the TDC illustrated in FIG. 3A, each parameter is to be calculated based on the peak P1 of higher signal intensity. That is, in the conventional parametric imaging, it has been difficult to render a color image by each parameter based on the peak P2 of weaker signal intensity than the peak P1. In the actual clinical practice, however, there are situations in which the information on the peak P2 is useful, and there are cases in which the observer desires to observe a color image based on the peak P2. For example, in a case of stroke, tissues are imaged late, and thus the observation of a color image concerning this is desirable. In a case after a coil treatment of cerebral aneurysm, there are cases in which deeper tissues in the aneurysm are imaged at a significantly late timing, as compared with main blood vessels, for example, and thus the observation of a color image concerning this is desirable. As just described, the observation of a color image is desirable for the delayed imaging in which the contrast material is visible weakly-stained at a later time as compared with main blood vessels. In the conventional technology, however, there are some limitations in rendering the image, and there have been cases in which it is difficult to display it.

In the conventional technology, it is possible to define the frames (or the time) to allocate the color information in any range. However, because there is no difference in the peak that is the target of calculating the parameter values, it is difficult to display a color image based on the second peak of weaker signal intensity. FIG. 3B (A) illustrates a color image of the TTP when the color information was allocated to the first to the 60th frames out of the 86 frames, and FIG. 3B (B) illustrates a color image of the TTP when the color information was allocated to the 60th to 86th frames out of the 86 frames. For example, as illustrated in FIG. 3B (A), in the situation in which the color information was allocated to the first to the 60th frames, blood vessels that indicate a maximum value of signal intensity near the 30th frame are clearly rendered. However, in the situation in which the color information was allocated to the 60th to 86th frames, as illustrated by the arrow in FIG. 3B (B), the blood vessels for which the signal intensity reaches a maximum value near the 30th frame are not colorized. That is, even when the frames (or the time) to allocate the color information are defined in an arbitrary range, because the peak to calculate the parameter values is the same, it is difficult to display a color image that is based on the second peak of weaker signal intensity in the blood vessel region pointed by the arrow.

Figure 4:
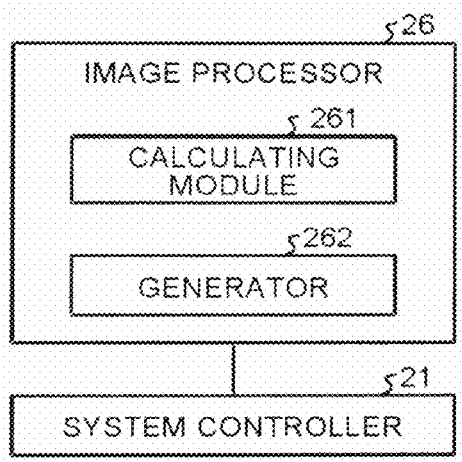
FIG. 4 is a block diagram illustrating one example of the configuration of an image processor in the first embodiment.

Consequently, the X-ray diagnostic apparatus 100 in the present application is configured to improve the rendering of an image by parametric imaging by allowing a section, which is the target of calculating the parameter values, in the TDC of the contrast-enhanced images to be defined. FIG. 4 is a block diagram illustrating one example of the configuration of the image processor 26 in the first embodiment. As illustrated in FIG. 4, the image processor 26 in the first embodiment includes a calculating module 261 and a generator 262, and performs a variety of processing under the control of the system controller 21.

The calculating module 261 calculates, based on the temporal transition in the signal intensity of the contrast material in a predetermined section of a plurality of X-ray images radiographed with time by using the contrast material, feature quantity in the flow of the contrast material for each pixel. Specifically, the calculating module 261 extracts, in the transition in the signal intensity of the contrast material, a section corresponding to a single increase and decrease in the signal intensity as a predetermined section out of a plurality of increases and decreases in the signal intensity, and calculates the parameter values for each pixel based on the increase and decrease in the signal intensity included in the extracted section. At this time, the calculating module 261 extracts a plurality of sections corresponding to the respective increases and decreases in the signal intensity, and calculates the parameter values for each pixel in the respective extracted sections.

The contrast-enhanced image processed by the calculating module 261 is a difference image that is obtained by differencing the images of before and after the contrast-imaging. For example, the image processor 26 generates a difference image (for example, a DSA image) that is obtained by performing the subtraction of a mask image that was radiographed in a state of the contrast material not being injected from a contrast image that was radiographed in a state of the contrast material being injected. The image processor 26 generates a difference image for each frame radiographed for a predetermined radiographing time and at a predetermined frame rate. That is, the image processor 26 performs the subtraction with the mask image for each of a plurality of contrast images that are radiographed while the contrast material is flowing. The frame here is equivalent to an image. The frame rate means the number of frames radiographed per unit time.

By using one frame immediately before the administration of the contrast material as a mask image, the image processor 26 can reduce a mistake in positioning (registration) attributable to body movement to a minimum. The image processor 26 can further perform noise reduction processing with image processing filters such as a moving average (smoothing) filter, a Gaussian filter, and a median filter. That is, the image processor 26 can perform a pre-treatment including positional deviation correction and noise removal to each of a group of a plurality of X-ray images radiographed with time by using the contrast material.

The calculating module 261 calculates, based on the TDC of a predetermined section in the difference image of each frame generated as in the foregoing, parameter values in the flow of the contrast material for each pixel. The calculating module 261 determines a boundary of a plurality of increases and decreases in signal intensity, by using the temporal transition in the signal intensity of the contrast material in a blood vessel region included in a plurality of X-ray images radiographed with time by using the contrast material and the temporal transition in the signal intensity of the contrast material in a non-blood vessel region included in the X-ray images, and then based on the determined boundary, extracts a section corresponding to a single increase and decrease as a predetermined section out of the increases and decreases, for example.

FIG. 5 is a diagram for explaining one example of extracting a section by the calculating module 261 in the first embodiment. For example, as illustrated in FIG. 5 (A), the calculating module 261 extracts a TDC 1 of a pixel representing a blood vessel 53 that is included in the images and a TDC 2 of a pixel representing a non-blood vessel region. The calculating module 261 then determines, to be a boundary, a point at which the extracted TDC 1 and the TDC 2 intersect with each other, and determines a section by using the determined boundary. The calculating module 261 determines, to be the boundary of peaks, the position of intersection when the TDC 1 in the blood vessel region and the TDC 2 in the non-blood vessel region are aligned in chronological order and are superimposed after the maximum values of the respective signal intensities are normalized.

That is, after normalizing (for example, making maximum values be the same value) a peak P3 of the TDC 1 of the pixel representing the blood vessel 53 and a peak P4 of the TDC 2 of the pixel representing the non-blood vessel region, the calculating module 261 determines the position of intersection to be the boundary. The calculating module 261 then extracts, by using the determined boundary, a section that is the target of calculating the parameter values in the radiographed contrast-enhanced images as "time or frame: a-b" as illustrated in FIG. 5 (A). The calculating module 261 then calculates the parameter values for the section determined in time or frames in the TDC of the contrast-enhanced images. For example, as illustrated in FIG. 5(B), the calculating module 261 calculates the respective parameter values based on the signal intensity in the section "a-b" in the TDC of the contrast-enhanced images. Consequently, the calculating module 261 can calculate the respective parameter values based on the peak P2 out of the peak P1 and peak P2 of the TDC. In the same manner, the calculating module 261 can calculate the respective parameter values based on the peak P1 with the section for which the time or frames are prior to "a" as the target of calculating the parameter values.

In FIG. 5, explained has been the situation in which a boundary is determined from the TDC of a pixel of a blood vessel and the TDC of a pixel in a non-blood vessel region. However, the embodiment is not limited to this, and it may be a situation in which a boundary is determined from the TDC of the average of a plurality of pixels included in the blood vessel region and the TDC of the average of a plurality of pixels included in the non-blood vessel region. In such a case, the calculating module 261 calculates the average TDC by calculating, for each frame, the average of the signal intensity in the blood vessel region and the average of the signal intensity in the non-blood vessel region.

As in the foregoing, the calculating module 261 determines a boundary from the TDC of a blood vessel region and the TDC of a non-blood vessel region in the images, and extracts a section. The calculating module 261 extracts a blood vessel region and a non-blood vessel region from the images by using a number of methods. The following describes in sequence the methods to extract a blood vessel region, and the methods to extract a non-blood vessel region.

For example, the calculating module 261 extracts a blood vessel region by the following three methods. As the first method, the calculating module 261 extracts, as a blood vessel region, a region for which the arrival time of the contrast material is early in a plurality of X-ray images. For example, the calculating module 261 calculates the values of the parameter "AT" in the TDC of the respective pixels in the contrast-enhanced images. The calculating module 261 then extracts the pixels that indicate low values out of the calculated values of "AT" of the respective pixels (pixels of fast rise in signal intensity), as the pixels of a blood vessel region. The calculating module 261 extracts a predetermined number of pixels (for example, 100) in order of low value as the pixels of the blood vessel region.

Next, the second method will be described. As the second method, the calculating module 261 calculates the TDC in high-frequency images included in a plurality of X-ray images as the TDC of the blood vessel region. For example, the calculating module 261 generate high-frequency images indicative of the region in which the pixel value is drastically changed, by applying a high-pass filter to the contrast-enhanced images. The calculating module 261 then extracts the pixels of the region in which the value is drastically changed in the generated high-frequency images, as the pixels of the blood vessel region. That is, the calculating module 261 detects the edges of the blood vessel region that is heavily stained by the contrast material, and extracts the blood vessel region from the detected edges.

Next, the third method will be described. As the third method, the calculating module 261 calculates, based on the region of interest defined in a blood vessel region included in a plurality of X-ray images, the temporal transition in the signal intensity of the contrast material in the blood vessel region. That is, the calculating module 261 extracts the region designated by the operator as the blood vessel region. For example, when the parametric imaging in which the parameter values based on the TDC of a predetermined section in the TDC is reflected is performed, the input module 22 receives an operation of designating the blood vessel region for the contrast-enhanced images displayed on the display module 23. The calculating module 261 extracts, based on the operation of designating the blood vessel region received by the input module 22, the blood vessel region in the contrast-enhanced images.

In the foregoing, the extraction of a blood vessel region has been described. Next, the cases of extracting a non-blood vessel region will be described. For example, the calculating module 261 extracts a non-blood vessel region by the following three methods. As the first method, the calculating module 261 extracts, as a non-blood vessel region, the region other than the blood vessel region extracted based on the value of "AT." Alternatively, the calculating module 261 extracts the pixels that indicate high values of "AT" (pixels of slow rise in signal intensity), as the pixels of the non-blood vessel region. That is, the calculating module 261 extracts the region of not being the blood vessel region, as the non-blood vessel region.

Next, the second method will be described. As the second method, the calculating module 261 calculates the TDC in low-frequency images included in a plurality of X-ray images as the TDC of the non-blood vessel region. For example, the calculating module 261 generates low-frequency images indicative of the region in which the change in pixel value is smooth, by applying a low-pass filter to the contrast-enhanced images. The calculating module 261 then extracts the pixels of the region in which the value is smoothly changed in the generated low-frequency images, as the pixels of the non-blood vessel region.

Next, the third method will be described. As the third method, the calculating module 261 calculates, based on the whole of the radiographed subject included in a plurality of X-ray images or the region of interest of a predetermined size defined in the images, the TDC of the non-blood vessel region. That is, the calculating module 261 extracts the region designated by the operator as the non-blood vessel region. For example, when the parametric imaging in which the parameter values based on the TDC of a predetermined section in the TDC is reflected is performed, the input module 22 receives an operation of designating the region for the contrast-enhanced images displayed on the display module 23. The input module 22 receives an operation of designating a region in a size exceeding a predetermined size. The calculating module 261 calculates the TDC of the average of the designated region as the TDC of the non-blood vessel region. That is, because the ratio of the blood vessels that occupy the contrast-enhanced images is not much high, designating the region of a large size and calculating the TDC of the average of the designated region are to calculate the TDC of the non-blood vessel region in which the majority is the portion other than the blood vessels. Note that the background in the contrast-enhanced images is removed beforehand.

Figure 6:
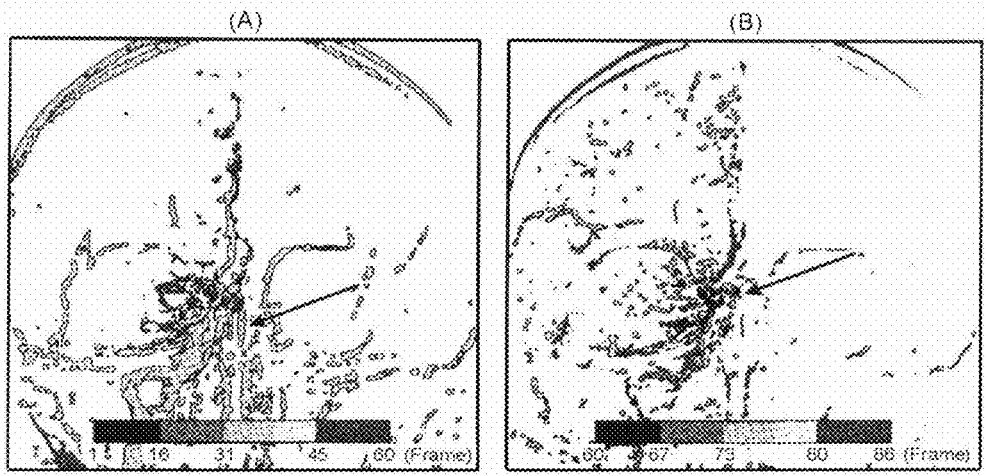
FIG. 6 is a diagram illustrating examples of color images generated by a generator in the first embodiment.

Referring back to FIG. 4, the generator 262 generates an image in which the feature quantity for each pixel calculated by the calculating module 261 is reflected in the pixel. Specifically, the generator 262 converts the information on the feature quantity, which is calculated based on the temporal transition in the signal intensity of the contrast material in a predetermined section, into an upper limit and a lower limit of color information to colorize the X-ray images, and generates a color image in which the converted color information is reflected in each pixel in the X-ray images. For example, the generator 262 generates a plurality of color images based on the feature quantity calculated in a plurality of sections. The system controller 21 then displays the images generated by the generator 262 on the display module 23. FIG. 6 is a diagram illustrating examples of the color images generated by the generator 262 in the first embodiment. In FIG. 6, illustrated are the situations in which the processing was performed on the contrast-enhanced images of 86 frames in total illustrated in FIG. 2B.

For example, when the calculating module 261 determines the frame "60" to be a boundary for the contrast-enhanced images of 86 frames in total and calculates the respective parameter values in the section "1-60" of the TDC and the respective parameter values in the section "60-86" of the TDC, the generator 262 generates the color images illustrated in FIG. 6. That is, the generator 262 generates the image in FIG. 6 (A) as a color image concerning the section "1-60" and generates the image in FIG. 6B as a color image concerning the section "60-86."

The generator 262 allocates colors to 60 frames of the first to the 60th and generates a color image in which the colors corresponding to the respective parameter values for each pixel calculated by the calculating module 261 are reflected in the respective pixels, for example. In one example, as illustrated in FIG. 6 (A), the generator 262 generates a color image in which the respective pixels are colorized with the color corresponding to the "TTP" value of "frame that reached a peak" in the section "1-60" of the TDC.

In the same manner, the generator 262 allocates colors to 27 frames of the 60th to 86th and generates a color image in which the colors corresponding to the respective parameter values for each pixel calculated by the calculating module 261 are reflected in the respective pixels, for example. In one example, as illustrated in FIG. 6B, the generator 262 generates a color image in which the respective pixels are colorized with the color corresponding to the "TTP" value of "frame that reached a peak" in the section "60-86" of the TDC.

Consequently, as illustrated in FIG. 6, the color image (FIG. 6 (A)) generated with the parameter values based on the peaks included in the section "1-60" and the color image (FIG. 6 (B)) generated with the parameter values based on the peaks included in the section "60-86" can be displayed. That is, as indicated by the arrows in FIG. 6, the color images of the identical position based on different peaks can be clearly rendered. In other words, the parametric imaging concerning low peaks that were not possible to render conventionally can be performed. The two of the image illustrated in FIG. 6 (A) and the image illustrated in FIG. 6 (B) are displayed automatically after the processing of the parametric imaging is finished.

FIG. 7 is a diagram illustrating one example of the parametric imaging in the first embodiment. In FIG. 7, FIG. 7 (A) illustrates a color image in which colors are simply allocated to the frames "60-86" (an example of the conventional technology) in the contrast-enhanced images of 86 frames in total, and FIG. 7 (B) illustrates a color image in which the parameter "TTP" is calculated by using the values of the frames "60-86" in the TDC of the contrast-enhanced images and colorized. The TDC illustrated in the lower portion in FIG. 7 represents the TDC of the average of the pixels included in a region R1.

For example, in the conventional technology, because the colors are simply allocated to the frames "60-86", the value of the parameter "TTP" calculated based on the maximum peak near the 42nd frame is not reflected, and as illustrated in FIG. 7 (A), the inside of the region R1 is hardly colorized. In contrast, in the color image generated by the generator 262, the values of the parameter "TTP" calculated based on the second peak (around the 62nd frame) in the TDC of the region R1 are reflected. For example, a color image in which the tissues that are imaged late in a case of stroke are colorized can be displayed. As in the foregoing, in the X-ray diagnostic apparatus 100 in the present application, the rendering of the image by the parametric imaging can be improved.

Figure 8D:
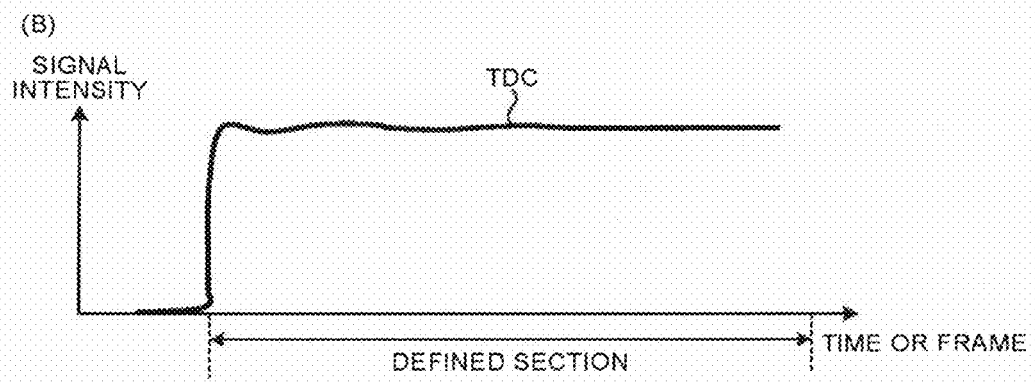
FIG. 8D is a diagram for explaining an application example of the X-ray diagnostic apparatus in the first embodiment.

With reference to FIGS. 8A to 8D, the following describes application examples in the first embodiment. FIGS. 8A to 8D are diagrams for explaining the application examples of the X-ray diagnostic apparatus 100 in the first embodiment. For example, as illustrated in FIG. 8A (A), the X-ray diagnostic apparatus 100 in the first embodiment can be applied to radiographing after a coil treatment of cerebral aneurysm. As in the foregoing, in a case after the coil treatment of cerebral aneurysm, there are cases in which deeper tissues in the aneurysm are imaged at a significantly late timing, as compared with a main blood vessel. Thus, depending on the angle of radiographing, the cerebral aneurysm may overlap with the main blood vessel and other blood vessels, and there are cases in which checking the state of blood flow in the aneurysm is difficult. Consequently, by applying the X-ray diagnostic apparatus 100 in the first embodiment, and performing the parametric imaging for which a section is defined at a latter half of the TDC as illustrated in FIG. 8A (B), a color image in which the state of blood flow in the aneurysm is rendered can be observed.

Furthermore, as illustrated in FIG. 8B, the X-ray diagnostic apparatus 100 in the first embodiment can also be applied to radiographing cerebral arteriovenous malformation (AVM), for example. In the AVM, the anomalous anastomosis of arteries and veins is formed in blood vessels of the brain, and it provides the cause of a subarachnoid hemorrhage and a brain hemorrhage. Thus, for the AVM, a treatment such as embolization with a high-concentration solution is performed. In the AVM, because the blood vessels run intricately, the blood vessels are imaged significantly late depending on the location in some cases, and thus there are cases in which it is difficult to observe the state of blood flow in the AVM. Consequently, by applying the X-ray diagnostic apparatus 100 in the first embodiment, and performing the parametric imaging for which a section corresponding to the AVM is defined as illustrated in FIG. 8B (B), a color image in which the state of blood flow in the AVM is rendered can be observed.

As illustrated in FIG. 8B (B), when there are three peaks (artery, AVM, and vein) present in the TDC, the calculating module 261 calculates, for example, the TDCs of two blood vessel regions by extracting the pixels in the respective blood vessel regions in normal and reverse chronological order, and calculates the TDC of the pixels in the non-blood vessel region. The calculating module 261 then determines two boundaries by using the three calculated TDCs, and by using the two determined boundaries, extracts three sections. As for the extraction of pixels in the blood vessel region in reverse chronological order, when the contrast-enhanced images are arranged in reverse chronological order, the pixels in the region for which the arrival of the contrast material is early (pixels of low values of the parameter "AT") are extracted, for example.

Furthermore, as illustrated in FIG. 8C (A), the X-ray diagnostic apparatus 100 in the first embodiment can also be applied to radiographing an endoleak of a stent, for example. When a stent is indwelled at an aorta, for example, as indicated by the arrows in FIG. 8C (A), unless a portion between the stent and a blood vessel wall and a portion where a plurality of stents overlap are firmly attached, an endoleak in which the blood leaks from a gap may occur. When the stent is indwelled, whether such an endoleak is present is checked by injecting a contrast material. However, there are cases in which the leakage of blood (contrast material) by endoleak is slightly slow in terms of time and observed by a pale shade. In such a case, an experienced operator is hard to overlook such an endoleak. However, when an operator has not much experience or the display setting of the image is not appropriate, the endoleak is liable to be overlooked. Consequently, as illustrated in FIG. 8C (B), by applying the X-ray diagnostic apparatus 100 in the first embodiment, and performing the parametric imaging for which a section corresponding to the endoleak is defined at a latter half of the TDC, a color image in which the leakage by the endoleak is rendered can be observed.

Moreover, the X-ray diagnostic apparatus 100 in the first embodiment can also be applied to remove the influence of the body movement of a subject, for example. When a contrast material is administered into the body at the time contrast-enhanced images are radiographed, for example, it frequently occurs that the subject moves his/her body in surprise. When DSA images are treated, the movement of the subject appears as positional deviation between a mask image and a contrast image, and results in the noise in the image (hereinafter described as misregistration). Many of the cases in which such a misregistration occurs are immediately after administering the contrast material, and in the case of cerebral angiography, it is before and after when the main blood vessels begin to be stained. In the conventional technology, because the parameters are read from the start of radiographing, when the misregistration occurs even if it is of background tissue, the TDC may become as illustrated in FIG. 8D, for example, and the TDC may become as if the contrast material has been administered. Consequently, by applying the X-ray diagnostic apparatus 100 in the first embodiment, and defining the section subsequent to the movement of the subject as the target of defining section as illustrated in FIG. 8D, because the data before the movement of the subject is ignored, the parameter values having no influence of misregistration can be calculated. Because the subject often moves before the peak is reached in the main blood vessel, even when the section is limited, it has little influence to the final result.

Next, with reference to FIG. 9, the processing performed by the X-ray diagnostic apparatus 100 in the first embodiment will be described. FIG. 9 is a flowchart illustrating the procedure of processing performed by the X-ray diagnostic apparatus 100 in the first embodiment. As illustrated in FIG. 9, in the X-ray diagnostic apparatus 100 in the first embodiment, if it is in a parametric imaging mode (Yes at Step S101), the calculating module 261 determines whether it is in a section defining mode (Step S102).

If it is in the section defining mode (Yes at Step S102), the calculating module 261 extracts a blood vessel region and a non-blood vessel region (Step S103), and determines a boundary from the TDC of the blood vessel region and the TDC of the non-blood vessel region (Step S104). The calculating module 261 then defines a section based on the determined boundary (Step S105), and calculates parameter values from the TDC of the frames in the defined section (Step S106).

Subsequently, the generator 262 generates a color image based on the parameter values calculated by the calculating module 261 (Step S107). The system controller 21 then displays the color image generated by the generator 262 on the display module 23 (Step S108). In the determination at Step S102, if it is not in the section defining mode (No at Step S102), the calculating module 261 calculates the respective parameter values from the TDC of all of the frames, the generator 262 generates a color image, and the system controller 21 displays the generated color image on the display module 23 (Step S109). In the determination at Step S101, if it is not in the parametric imaging mode (No at Step S101), the generator 262 generates contrast-enhanced images and the system controller 21 displays the generated contrast-enhanced images on the display module 23 (Step S110).

As in the foregoing, in accordance with the first embodiment, the calculating module 261 calculates, based on the TDC of a predetermined section of a plurality of X-ray images radiographed with time by using a contrast material, parameter values in the flow of the contrast material for each pixel. The generator 262 generates an image in which the parameter values for each pixel calculated by the calculating module 261 are reflected in the pixel. The system controller 21 displays the image generated by the generator 262 on the display module 23. Consequently, the X-ray diagnostic apparatus 100 in the first embodiment can calculate the parameter values for each predetermined section and display an image in which the parameter values are reflected, making it possible to improve the rendering of the image by the parametric imaging.

Furthermore, in accordance with the first embodiment, the generator 262 converts the parameter information, which is calculated based on the TDC of a predetermined section, into an upper limit and a lower limit of color information to colorize the X-ray images, and generates a color image in which the converted color information is reflected in each pixel in the X-ray images. Consequently, the X-ray diagnostic apparatus 100 in the first embodiment can colorize and display the image, making it possible to improve the visibility.

In accordance with the first embodiment, the calculating module 261 extracts a section corresponding to a single peak in signal intensity as a predetermined section out of a plurality of peaks in signal intensity in the TDC, and calculates the parameter values for each pixel based on the peak in the signal intensity included in the extracted section. Consequently, the X-ray diagnostic apparatus 100 in the first embodiment calculates the parameter values for each peak included in the TDC, making it possible to display the image in which the respective parameter values are reflected.

In accordance with the first embodiment, the calculating module 261 determines a boundary of a plurality of peaks in signal intensity by using the TDC of a blood vessel region included in contrast-enhanced images and the TDC of a non-blood vessel region included in the contrast-enhanced images, and extracts, based on the determined boundary, a section corresponding to a single peak out of the peaks as a predetermined section. Consequently, the X-ray diagnostic apparatus 100 in the first embodiment makes it possible to extract an appropriate section.

In accordance with the first embodiment, the calculating module 261 determines, as a boundary of a plurality of peaks, the position of intersection when the TDC of a blood vessel region and the TDC of a non-blood vessel region are aligned in chronological order, and are superimposed after the maximum values of the respective signal intensities are normalized. Consequently, the X-ray diagnostic apparatus 100 in the first embodiment makes it possible to determine the boundary after correcting the deviation of boundary by the difference in the signal intensity.

In accordance with the first embodiment, the calculating module 261 extracts, as a blood vessel region, an region for which the arrival time of the contrast material is early in a plurality of X-ray images, and extracts, as a non-blood vessel region, the region different from the extracted blood vessel region. Consequently, the X-ray diagnostic apparatus 100 in the first embodiment makes it possible to extract the blood vessel region and the non-blood vessel region easily and accurately.

In accordance with the first embodiment, the calculating module 261 calculates the TDC in high-frequency images included in a plurality of X-ray images as the TDC of a blood vessel region. Consequently, the X-ray diagnostic apparatus 100 in the first embodiment makes it possible to calculate the TDC of the blood vessel region easily.

In accordance with the first embodiment, the calculating module 261 calculates the TDC in low-frequency images included in a plurality of X-ray images as the TDC of a non-blood vessel region. Consequently, the X-ray diagnostic apparatus 100 in the first embodiment makes it possible to calculate the TDC of the non-blood vessel region easily.

In accordance with the first embodiment, the calculating module 261 calculates, based on the region of interest defined in a blood vessel region included in a plurality of X-ray images, the temporal transition in signal intensity of a contrast material in the blood vessel region. Consequently, the X-ray diagnostic apparatus 100 in the first embodiment makes it possible to calculate the TDC of the blood vessel region accurately.

In accordance with the first embodiment, the calculating module 261 calculates, based on the whole of a radiographed subject included in a plurality of X-ray images or on the region of interest of a predetermined size defined on the X-ray images, the TDC of a non-blood vessel region. Consequently, the X-ray diagnostic apparatus 100 in the first embodiment makes it possible to calculate the TDC of the non-blood vessel region easily.

Second Embodiment

In the foregoing first embodiment, the situation of automatically defining a section in the contrast-enhanced images has been explained. In a second embodiment, a situation of receiving an operation of designating a section from the operator will be described. That is, in the second embodiment, the received content by the input module 22 is different. The following describes the second embodiment with a focus on this.

Figure 10:
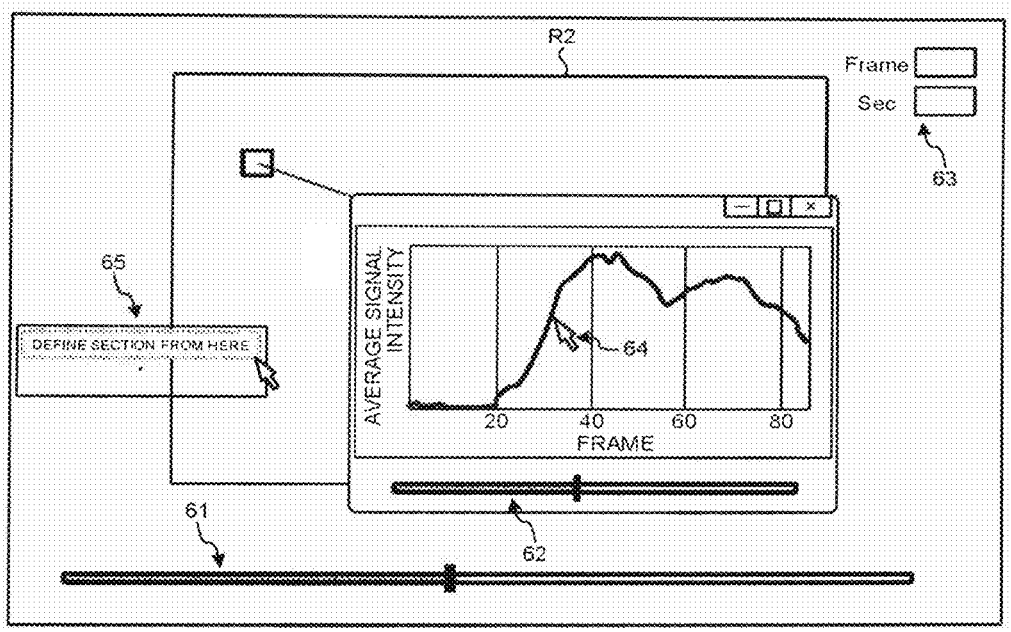
FIG. 10 is a diagram illustrating an example of a GUI that receives an operation of designating a section according to a second embodiment.

The input module 22 in the second embodiment receives an operation of designating, in the transition in signal intensity of a contrast material, a section corresponding to a predetermined increase and decrease in signal intensity out of a plurality of increases and decreases in signal intensity. Specifically, the input module 22 receives an operation of designating a section in a TDC that is the target of calculating parameter values. The calculating nodule 261 calculates, based on the signal intensity of the section received by the input module 22, the respective parameter values. The generator 262 then generates a color image based on the parameter values calculated by the calculating module 261, and the system controller 21 displays the color image on the display module 23. FIG. 10 is a diagram illustrating an example of a GUI that receives an operation of designating a section in the second embodiment. In FIG. 10, a plurality of GUIs are displayed on the same screen. In practice, however, the GUIs used can be determined in any combination.

For example, the input module 22 is, as pointed by an arrow 61 in FIG. 10, a slide bar on which a section is designated along the time axis. That is, the slide bar pointed by the arrow 61 is a GUI that can designate any time in the contrast-enhanced images displayed in an image display region R2. The operator can designate a section by performing a designating operation (for example, clicking) at a desired position while moving the time of the contrast-enhanced images displayed in the image display region R2 on the slide bar pointed by the arrow 61.

Furthermore, the input module 22 is, as pointed by an arrow 62 in FIG. 10, a slide bar on which a section is designated along the TDC, for example. That is, the slide bar pointed by the arrow 62 is a GUI that can designate any time in the TDC of any region (or pixel) in the contrast-enhanced images displayed in the image display region R2. The operator can designate a section by performing a designating operation (for example, clicking) at a desired position while moving the slide bar of the arrow 62 present within a window of the TDC displayed by designating any region (or pixel) in the contrast-enhanced images displayed in the image display region R2.

The input module 22, as pointed by an arrow 63 in FIG. 10, further receives the frame number or time of a plurality of X-ray images, for example. That is, the operator can designate a section by inputting a numerical value of the frame number or time in an input region of "Frame" or "Sec" pointed by the arrow 63.

The input module 22, as pointed by an arrow 64 in FIG. 10, further receives the designation of a section by being designated at a certain position on the TDC, for example. That is, the operator can designate a section at a desired position on the TDC with the pointer pointed by the arrow 64.

The input module 22, as pointed by an arrow 65 in FIG. 10, further receives the designation of a section by a GUI displayed on the image, for example. That is, the operator can designate a section by performing a right-clicking and the like on the contrast-enhanced images displayed in the image display region R2 to display a GUI such as "Define a section from here" pointed by the arrow 65, and clicking it at a desired timing, for example.

As in the foregoing, in accordance with the second embodiment, the input module 22 receives an operation of designating a section by various methods. Consequently, the X-ray diagnostic apparatus 100 in the second embodiment makes it possible to receive the operation of designating a section in accordance with the situation of the operator.

Third Embodiment

While the first and the second embodiments have been described above, the embodiments may be implemented in various different forms other than the foregoing first and second embodiments.

Figure 11A:
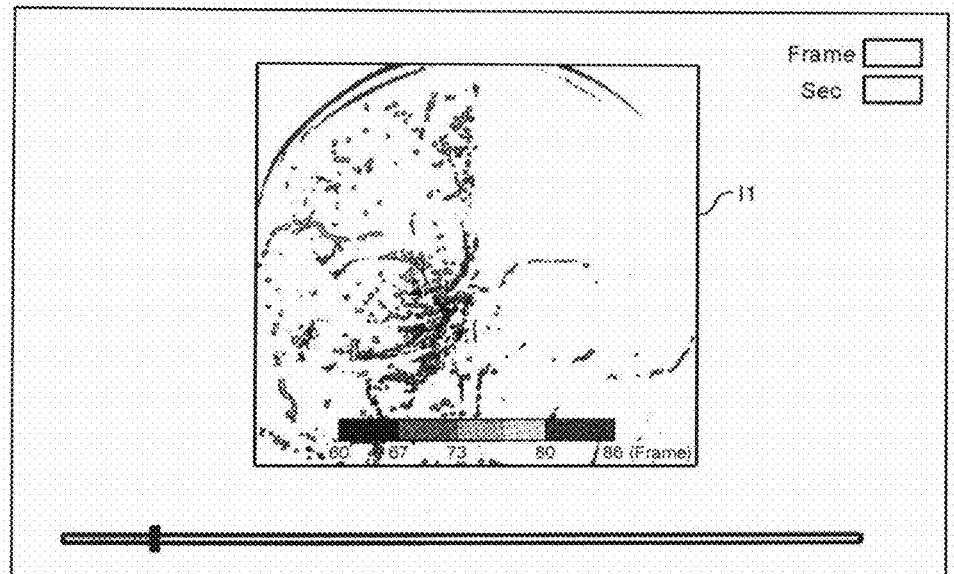
FIG. 11A is a diagram illustrating a display example of a color image according to a third embodiment.
Figure 11B:
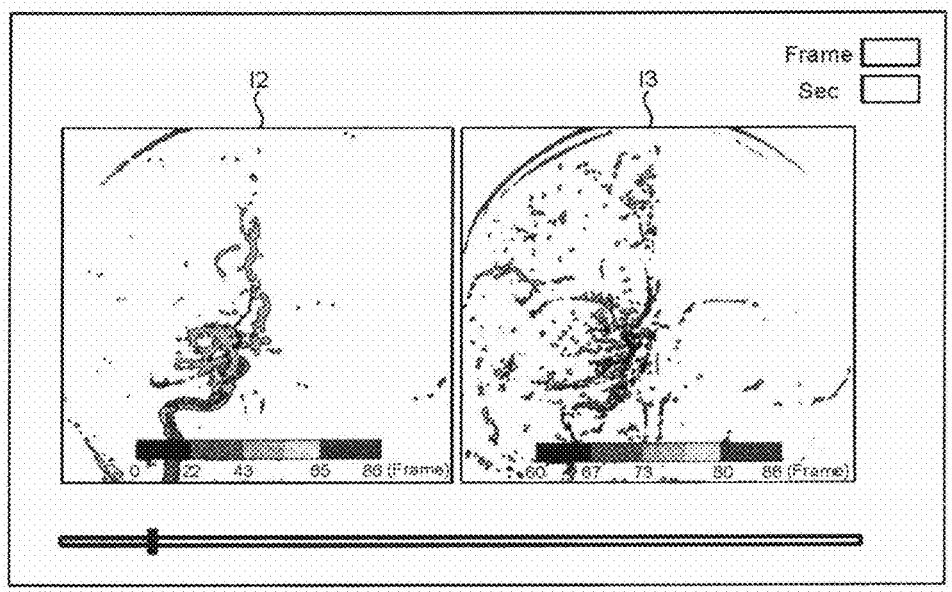
FIG. 11B is a diagram illustrating a display example of color images in the third embodiment.
Figure 11C:
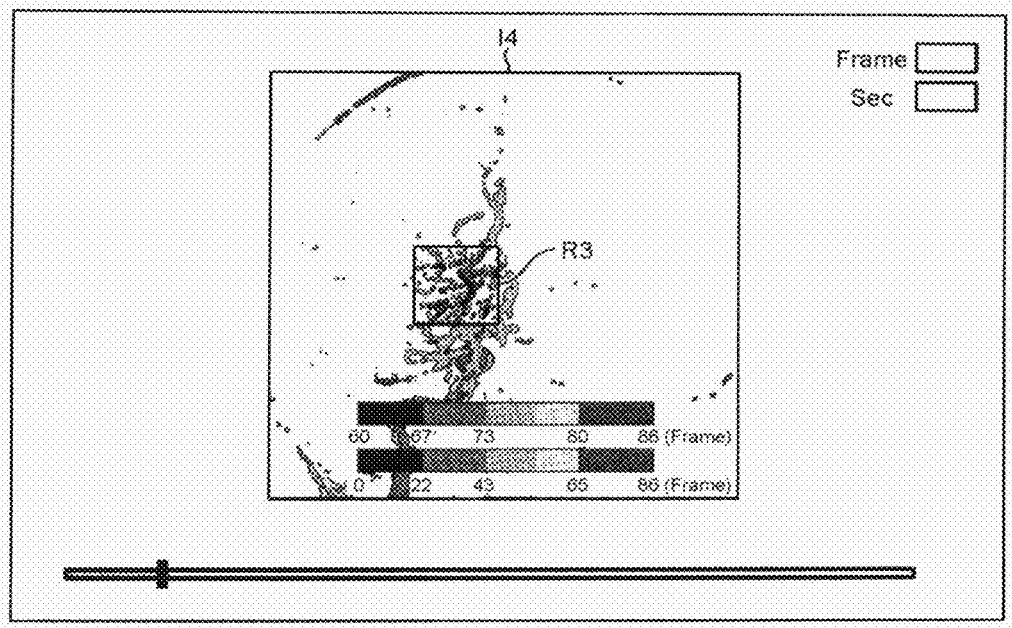
FIG. 11C is a diagram illustrating a display example of a color image in the third embodiment.

The color images described in the foregoing embodiments can be displayed in various forms on the display module 23. FIGS. 11A to 11C are diagrams illustrating display examples of the color images according to a third embodiment. For example, as illustrated in FIG. 11A, the system controller 21 displays, on the display module 23, only a color image I1 generated with the parameter values calculated based on the TDC of a predetermined section for example, "60-86"). Furthermore, as illustrated in FIG. 11B, the system controller 21 displays, on the display module 23, both a color image I2 generated with the parameter values calculated based on the TDC of all frames and a color image I3 generated with the parameter values calculated based on the TDC of a predetermined section (for example, "60-86"), for example.

Moreover, as illustrated in FIG. 11C, the system controller 21 displays, on the display module 23, a color image I4 in which a color image generated with the parameter values calculated based on the TDC of a predetermined section (for example, "60-96") is embedded (or superimposed) in an region R3 of a color image generated with the parameter values calculated based on the TDC of all frames, for example. In such a case, for example, by designating any region in the color image generated with the parameter values calculated based on the TDC of all frames by the operator via the input module 22, the inside of the image display region R3 is replaced with a color image generated with the parameter values calculated based on the TDC of a predetermined section. When the color image is embedded or superimposed, as illustrated in FIG. 11C, a color bar corresponding to the section "60-86" is newly displayed. While the color bar for the embedded (or superimposed) color image is displayed as a separate color bar, as illustrated in FIG. 11C, the operator can switch it to display or non-display optionally. The display region for a single color bar may be provided even when the color image is embedded or superimposed, and it may be configured to display the color bar corresponding to the portion indicated by a pointer by switching.

The shape of the region to replace is not limited to a rectangle illustrated in FIG. 11C, and it may be replaced in any shape. Furthermore, as for the region to replace, it may be configured to replace the image for each radiographed region. For example, it may be a case of generating and displaying an image in which, when the sections are defined in three phases of arteries, tissues, and veins and the respective parameter values are calculated, the positions on the color image that is generated based on the parameter values calculated with all frames as the target are replaced with the respective images.

That is, it may be a case of generating and displaying an image in which, in the color image generated based on the parameter values calculated with all frames as the target, the position of the arteries is replaced with a color image that is based on the parameter values calculated with the peak of the arteries, the position of the tissues is replaced with a color image that is based on the parameter values calculated with the peak of the tissues, and the position of the veins is replaced with a color image that is based on the parameter values calculated with the peak of the veins.

Furthermore, in the above-described second embodiment, the situations of receiving the designation of a section via the GUI have been described. The embodiment, however, is not limited to this, and it may be a situation of receiving the designation of a section by voice, for example. In such a case, the operator designates a section by voice while observing a moving image of the contrast-enhanced images, for example.

Moreover, in the foregoing first and second embodiments, described have been the situations of generating a color image by calculating the respective parameter values based on the peak in the defined section. However, a maximum value of the peak included in the defined section is not always the highest value in the section. For example, when a section is defined for a small peak located next to a large peak, if the boundary is closer to the large peak side, there are cases in which the signal intensity of the boundary is higher than the small peak. In such a case, the respective parameter values are calculated based not on the small peak but on the value of the boundary on the large peak side, and thus an accurate image cannot be rendered.

Consequently, in the X-ray diagnostic apparatus 100 according to the third embodiment, the calculating module 261 determines for each pixel, when calculating the parameter values in the flow of the contrast material for each pixel based on the TDC of a predetermined section, whether the maximum value of signal intensity is of an end portion of the predetermined section. When the maximum value of signal intensity is determined to be of the end portion of the predetermined section by the calculating module 261, the generator 262 generates the information indicating that the pixel is of a singular value. The system controller 21 then displays the information indicative of the singular value on the display module 23.

FIG. 12 is a diagram for explaining one example of processing performed by the X-ray diagnostic apparatus 100 in the third embodiment. For example, as illustrated in the upper portion in FIG. 12, when the calculating module 261 extracts a section "c-d" (or the section "c-d" is designated) of the TDC of the contrast-enhanced images, the calculating module 261 determines whether a maximum value of signal intensity in the section "c-d" is of the end portion "c" or "d" of the section "c-d." As illustrated in FIG. 12, because the maximum value in the section "c-d" is of the end portion "c," the calculating module 261 notifies the generator 262 of the information that the parameter value to calculate is a singular value.

The calculating module 261 then calculates respective parameter values based on the value of the end portion "c" that is the maximum value, or calculates the respective parameter values based on a local peak. That is, when the calculating module 261 determines that the maximum value of signal intensity is of the end portion of the predetermined section, the calculating module 261 extracts the peak in the predetermined section, and based on the extracted peak, calculates the respective parameter values. For example, as illustrated in the lower portion in FIG. 12, the calculating module 261 extracts a peak (local peak) in the section "c-d" and calculates the respective parameter values based on the value "e" of the extracted peak. Then, the calculating module 261 further notifies the generator 262 of the information that the calculated respective parameter values are based on the value of the end portion or based on the value of the local peak.

When the generator 262 receives the notice of being a singular value from the calculating module 261, the generator 262 generates information indicating that a singular value is included in the generated color image. For example, when the respective parameter values are based on the value of the end portion, the generator 262 does not colorize the appropriate pixels and generates an image that indicates the pixels in black (or in a color designating a singular value). When the respective parameter values are based on the value of the local peak, the generator 262 generates an image indicative of being a singular value by colorizing the pixels in the colors corresponding to the parameter values and making the colors lighten, for example.

The system controller 21 displays the image generated by the generator 262 on the display module 23. Consequently, the operator can easily recognize that a singular value is included in the image. As for whether a singular value is included, it may be configured to display not only the rendered image but also such information when a pointer is positioned over the pixel for which the parameter values are of a singular value, for example.

In the above-described first and second embodiments, the situation of using the "TTP" as the parameter has been explained. The embodiment, however, is not limited to this, and it may be a situation in which a color image is generated by using other parameters such as "PH" and "AUC," for example.

In the above-described first and second embodiments, the situation of rendering the difference in parameter values by hue has been explained. The embodiment, however, is not limited to this, and it may be a situation in which the lightness of colors such as red and blue is changed or a situation in which a grayscale that represents the contrast from black to white is used, for example.

Furthermore, in the foregoing first and second embodiments, explained has been the situation in which a color image corresponding to parameter values is displayed by arbitrarily defining a section that is the target of calculating the parameter values in the TDC of the contrast-enhanced images, and allocating colors to the defined section. The embodiment, however, is not limited to this, and it may be a situation in which a color image that corresponds to the parameter values in any section is generated and displayed while the allocation of colors is kept constant, for example. Explaining by using the example in the first embodiment, colors are allocated to 86 frames of 1 to 86, for example, and by using the allocated colors, color images corresponding to the parameter values in the respective sections "1-60" and "60-86" of the TDC are generated. The following describes the above-described first and second embodiments in detail.

Specifically, the calculating module 261 calculates, based on the temporal transition in signal intensity of a contrast material in a predetermined section of a plurality of X-ray images radiographed with time by using the contrast material, the feature quantity concerning the flow of the contrast material for each pixel in the predetermined section. The generator 262 generates a first color image in which color information corresponding to the feature quantity concerning the flow of the contrast material in a first section as the predetermined section is reflected in each pixel. The system controller 21 changes the predetermined section to a second section that is within the first section. When the predetermined section is changed to the second section, the generator 262 generates, based on the color information corresponding to the second section out of the color information corresponding to the feature quantity concerning the flow of the contrast material in the first section, and the feature quantity calculated in the second section, a second color image in which the color information corresponding to the feature quantity concerning the flow of the contrast material in the second section is reflected in each pixel. The calculation of the feature quantity concerning the flow of the contrast material in the second section is performed in the same manner as the above-described calculation of the feature quantity.

Figure 13:
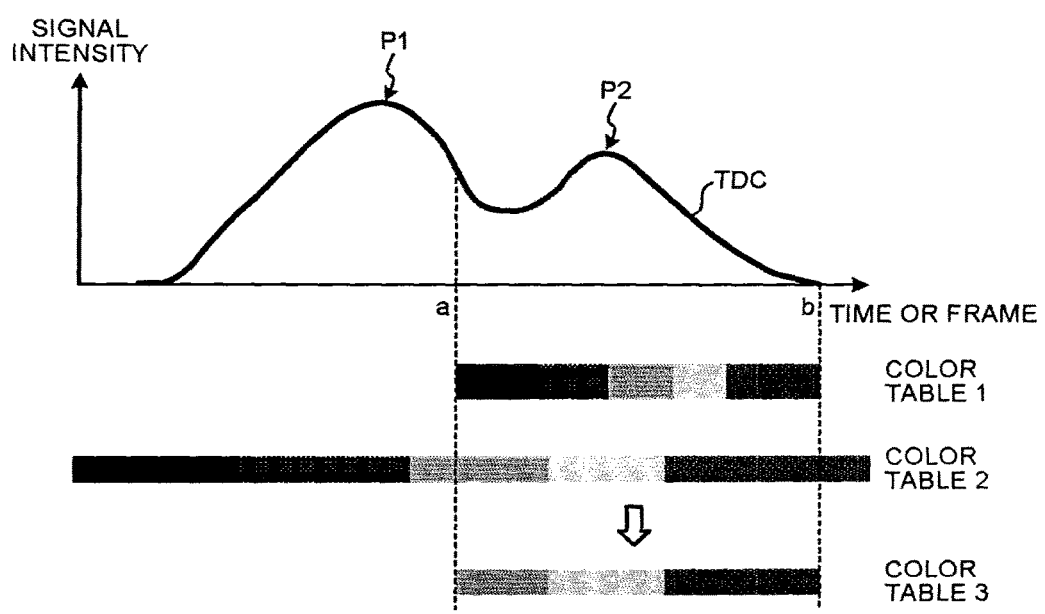
FIG. 13 is a diagram for explaining color-image generation processing performed in the third embodiment.

FIG. 13 is a diagram for explaining color-image generation processing performed in the third embodiment. In FIG. 13, illustrated are a color table 1 used for color image generation in the first and the second embodiments and color tables 2 and 3 used for color image generation in the third embodiment. Furthermore, in FIG. 13, illustrated is a situation in which the calculating module 261 calculated the respective parameter values based on the signal intensity in the section "a-b" in the TLC of the contrast-enhanced images. First, the color image generation in the first and the second embodiments will be described again. For example, as illustrated in FIG. 13, when the calculating module 261 calculates the parameter values based on the peak P2 included in the section "a-b," the generator 262 in the first and the second embodiments generates the color table 1 in which all colors are allocated to the time or the frames in the section "a-b" and generates a color image by using the generated color table 1. That is, the generator 262 in the first and the second embodiments performs parametric imaging by the parameter values based on the peak P2 calculated by the calculating module 261 by using all of the colors. In other words, each time a section is defined, the generator 262 in the first and the second embodiments generates a color table in which all of the colors are allocated to the time or frames in the section and generates a color image by using the generated color table.

Meanwhile, as illustrated in FIG. 13, for example, the generator 262 in the third embodiment extracts, out of the color table 2 in which all of the colors are allocated to the time or the frames of the whole section of the contrast-enhanced images, a color table for a defined section and generates a color image based on the extracted color table. For example, the generator 262 generates a color image by using the color table 3 corresponding to the section "a-b" in the color table 2. That is, the generator 262 in the third embodiment acquires the colors corresponding to the parameter values based on the peak P2 calculated by the calculating module 261 for each pixel from the color table 3 and performs the parametric imaging in which the acquired colors are reflected in the respective pixels.

The color table 2 may be used regardless of when it is generated. For example, when the parametric imaging by the parameter values in the section "a-b" is performed, a color image by the parameter values for the whole section is generated first, and when the section "a-b" is subsequently defined, the color table 3 may be extracted by using the color table 2 generated at the time the color image by the parameter values for the whole section was generated. When the parametric imaging by the parameter values in the section "a-b" is performed without generating a color image by the parameter values for the whole section, the generator 262 may first generate the color table 2 in which all of the colors are allocated to the time or the frames of the whole section of the contrast-enhanced images, and extract the color table 3 from the generated color table 2.

In FIG. 13, described has been the situation in which the whole section of the contrast-enhanced images is used as the above-described first section. However, the embodiment is not limited to this, and it may be a situation in which a predetermined section in the whole section is defined as the first section. In one example, in the TDC based on the 86 frames of 1 to 86, it may be a case in which the section "10-80" is defined as the first section and the section "50-70" is defined as the second section. In such a case, the generator 262 generates a color table in which all of the colors are allocated to the frames "10-80", extracts a color table corresponding to the section "50-70" from the generated color table, and generates a color image.

Figure 14:
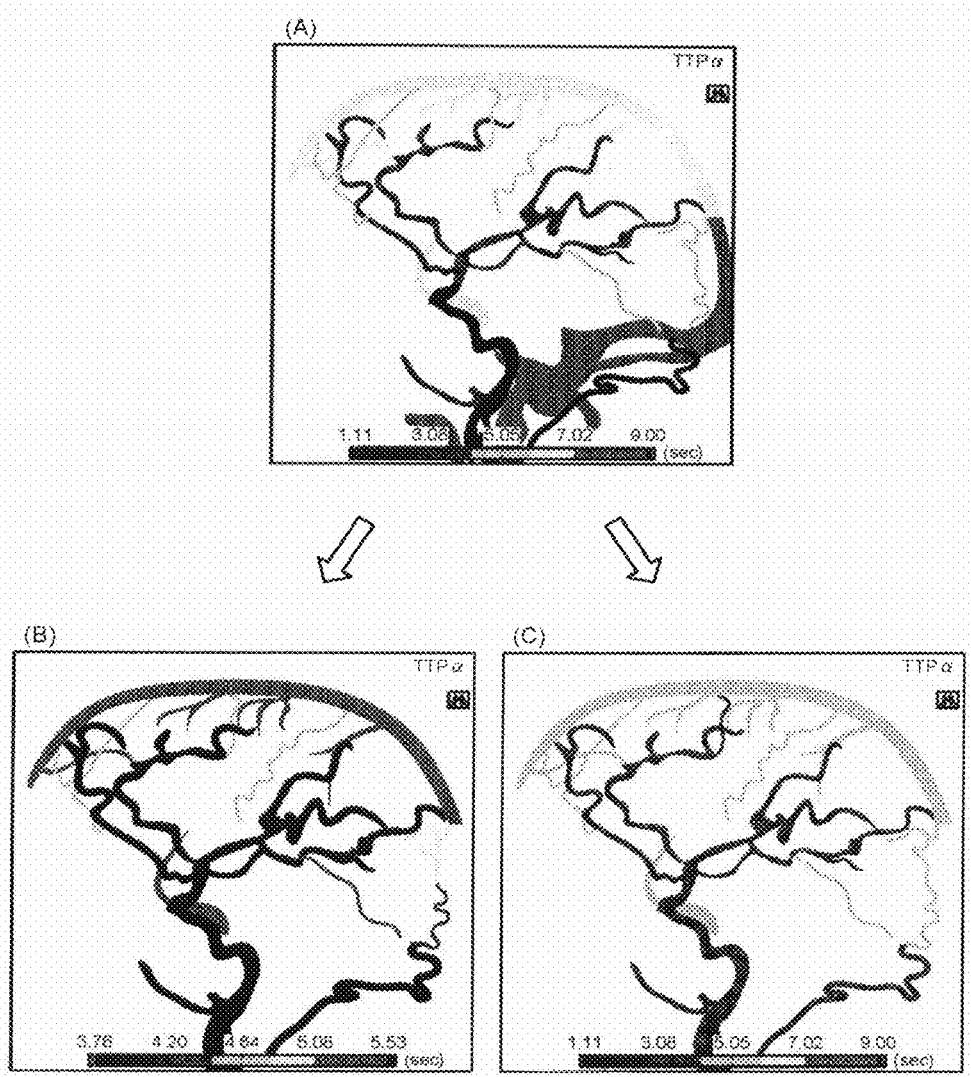
FIG. 14 is a diagram illustrating one example of color images in the third embodiment.

FIG. 14 is a diagram illustrating one example of color images in the third embodiment. In FIG. 14, illustrated is an example of a situation in which colors are allocated to the radiographed time of the contrast-enhanced images. In FIG. 14, illustrated are the result of the parametric imaging based on the parameter values of the time "1.11-9.00 (sec)" with colors allocated to the time "1.11-9.00 (sec)" (FIG. 14 (A)), the result of the parametric imaging in the first and second embodiments based on the parameter values of the time "3.76-5.53 (sec)" for the same contrast-enhanced images (FIG. 14 (B)), and the result of the parametric imaging in the third embodiment (FIG. 14 (C)).

For example, in the situation of the parametric imaging based on the parameter values of the time "1.11-9.00 (sec)" with colors allocated to the time "1.11-9.00 (sec)," as illustrated in FIG. 14 (A), a color image in which any of the colors are reflected in the whole of the region imaged at the time "1.11-9.00 (sec)" is generated. Now, when a color image based on the parameter values at the time "3.76-5.53 (sec)" of the TDC of the contrast-enhanced images is generated by the method in the first and the second embodiments, as illustrated in FIG. 14 (B), a color table in which all of the colors are allocated to the time "3.76-5.53 (sec)" is generated, and the color image is to be generated based on the color table. In such a case, as illustrated in FIG. 14 (B), the color image based on the parameter values at the time "3.76-5.53 (sec)" can be generated and the blood vessels that were overlapped and hidden become visible. However, the relation of the time and color is to be completely different from that in FIG. 14 (A).

For example, when the blood vessels imaged at the time "1.11-9.00 (sec)" change from arteries to capillaries and to veins, in FIG. 14 (A), the arteries are displayed in red, the capillaries are displayed in yellow to green, and the veins are displayed in blue. To observe the capillaries that are overlapped and hidden by arteries and veins, when a color image is generated by the method in the first and the second embodiments by defining the section to calculate the parameter values as "3.76-5.53 (sec)" and calculating the parameter values, the capillaries are represented by all of the colors of red to blue as illustrated in FIG. 14 (B), and thus there are cases in which the observer has difficulty in perceiving the blood vessels instinctively. That is, the observer is to observe the image while comparing the colors to the color bar indicated at the lower side of the image, and thus there are cases of deteriorating diagnostic efficiency.

However, when a color image is generated by the method in the third embodiment, as illustrated in FIG. 14 (C), a color image can be displayed in which the arteries and veins represented in FIG. 14 (A) are deleted and only the capillaries are represented. For example, when a color image is generated with the colors of "3.76-5.53 (sec)" in the color table indicated in FIG. 14 (C) by calculating the parameter values in the section "3.76-5.53 (sec)" of the TDC, as illustrated in FIG. 14 (C), the color image can be displayed in which the capillaries are represented in yellow to green. That is, the use of the method in the third embodiment enables the parametric imaging by using the parameter values of any section to the performed without changing the colors to represent arteries, capillaries, and veins, for example, and thus enables the diagnostic efficiency to be improved. For example, generating a color image by defining the section to calculate the parameter values as the time "1.11-3.00" and using the color of the time "1.11-3.00" (for example, red) out of the color table for which the colors are allocated to the time "1.11-9.00 (sec)" can delete capillaries and veins without changing the color of arteries.

As in the foregoing, in the X-ray diagnostic apparatus 100 in the third embodiment, by using a color table defined for the first section, the parametric imaging in the second section within the first section can be performed. The second section can be defined automatically in the same manner as a predetermined section in the foregoing. For example, the calculating module 261 may determine a boundary of a plurality of increases and decreases in signal intensity, by using the temporal transition in the signal intensity of the contrast material in a blood vessel region included in a plurality of X-ray images radiographed with time by using the contrast material and the temporal transition in the signal intensity of the contrast material in a non-blood vessel region included in the X-ray images, and then based on the determined boundary, extract a section corresponding to a single increase and decrease as the second section out of the increases and decreases. The calculating module 261 can extract a blood vessel region and a non-blood vessel region by any of the above-described methods.

Figure 15C:
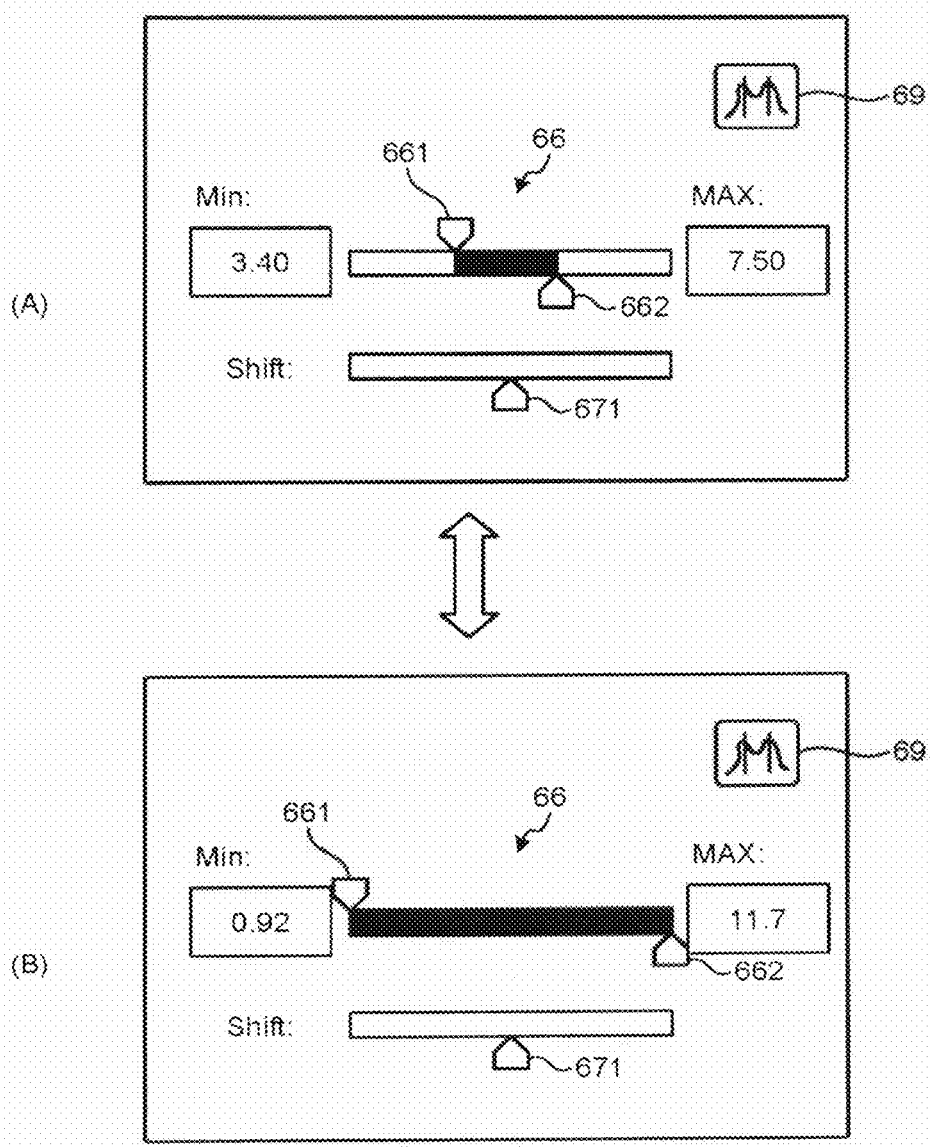
FIG. 15C is a diagram illustrating an example of the GUI that receives the operation of designating the second section in the third embodiment.

The second section may be in a situation of being defined by receiving an operation of designating a section from the operator. Specifically, the input module 22 receives an operation of designating the second section. The system controller 21 then controls the calculating module 261 and the generator 262 so as to perform the above-described processing with the section for which the designation operation was received by the input module 22 as the second section. FIGS. 15A to 15C are diagrams illustrating an example of a GUI that receives the operation of designating the second section in the third embodiment. In FIG. 15A, a plurality of GUIs are displayed on the same screen. In practice, however, the GUIs to use can be determined in any combination. In FIGS. 15A to 15C, illustrated is a situation in which the second section is defined with the time "0.92-11.70 (sec)" of the contrast-enhanced images radiographed with time as the first section.

For example, as illustrated in FIG. 15A, a window including an image display region R4 is provided with various GUIs, and displays a color image I5 and original contrast-enhanced images (such as DSA images) I6 and receives an operation of designating a section from the operator. In one example, as pointed by an arrow 66 in FIG. 15A, the input module 22 is a slide bar on which a predetermined section (second section) is designated by designating an end portion of the section along the time axis. For example, the operator designates, by operating the positions of a cursor 661 and a cursor 662 by using the input module 22 such as a mouse, the second section indicated in black on the slide bar. In one example, as illustrated in FIG. 15A, the operator defines the second section "3.4-7.5 (sec)" by moving the cursor 661 on the slide bar to the position of "Min: 3.4 (sec)" and moving the cursor 662 to the position of "Max: 7.5 (sec)."

As in the foregoing, when the input module 22 receives an operation of designating the second section "3.4-7.5 (sec)," the system controller 21 controls the calculating module 261 and the generator 262 so as to generate the color image I5 by the parameter values in the second section "3.4-7.5 (sec)." That is, the system controller 21 controls the calculating module 261 so as to calculate the parameter values in the second section "3.4-7.5 (sec)" of the TDC of the contrast-enhanced images. The system controller 21 then controls the generator 262 so as to generate the color image I5 by using colors corresponding to the second section "3.4-7.5 (sec)" out of the color table in which the colors are allocated to the time "0.92-11.70." The system controller 21 displays the color image I5 generated by the generator 262 on the image display region R4. The system controller 21 controls, each time the input module 22 receives an operation of designating a second section, the calculating module 261 and the generator 262 so as to generate a color image by the parameter values in the designated second section.

Furthermore, as pointed by an arrow 67 in FIG. 15A, the input module 22 is a slide bar on which a predetermined section (second section) is designated by moving a section of a predetermined width along the time axis, for example. Specifically, the slide bar pointed by the arrow 67 is a slide bar that simultaneously moves the cursor 661 and the cursor 662 while the current width is being kept, by moving a cursor 671 by the operator by using a mouse or the like. That is, the second section is defined by moving the cursor 661 and the cursor 662 of the slide bar pointed by the arrow 66 in conjunction with the movement of the slide bar pointed by the arrow 67.

For example, as illustrated in FIG. 15B (A), it is assumed that the cursor 661 of the slide bar pointed by the arrow 66 is at the position of "Min: 3.40 (sec)" and the cursor 662 is at the position of "Max: 7.50 (sec)." In such a case, when the operator moves the cursor 671, the cursor 661 and the cursor 662 are to move to the position corresponding to the movement of the cursor 671 while the width of "4.1 (sec)" is kept. In one example, as illustrated in FIG. 15B (B), in response to the movement of the cursor 671, the cursor 661 and the cursor 662 move to the position of "Min: 1.20 (sec)" and the position of "Max: 5.30 (sec)," respectively. Consequently, the second section is defined as "1.20-5.30 (sec)" and the parametric imaging in the defined second section "1.20-5.30 (sec)" is performed.

Referring back to FIG. 15A, the input module 22 receives an operation of designating a predetermined section (second section) by a plurality of X-ray images displayed on the display module 23, for example. In one example, as pointed by an arrow 68 in FIG. 15A, the operator defines a section by a mouse operation such as a right-clicking while observing the actual state of imaging represented by the original contrast-enhanced images (moving image) I6 displayed in the image display region. That is, the operator defines a second section by designating the start and end of the section at the desired time point while observing the moving image. While the situations of receiving the designation of the second section via the GUI have been described in the foregoing examples, it may be a situation of receiving the designation of the second section by voice.

As in the foregoing, when the second section is designated via the input module 22, a color image corresponding thereto is generated and displayed on the display module 23. It is also possible to display, by switching, a color image corresponding to the first section "0.92-11.70 (sec)" and a color image corresponding to the generated second section. For example, the system controller 21 displays, in the upper left region of the image display region R4, a color image corresponding to the first section "0.92-11.70 (sec)" and a color image corresponding to the second section, by switching each time a button 69 illustrated in FIG. 15A is depressed. That is, when the button 69 is depressed in a state illustrated in FIG. 15C (A) in which a color image corresponding to the second section is displayed, the section is switched to the first section "0.92-11.70 (sec)" and a color image corresponding to the first section is displayed on the display module 23 as illustrated in FIG. 15C (B). Meanwhile, when the button 69 is depressed in a state illustrated in FIG. 15C (B), the section is switched to the second section "3.4-7.5 (sec)" and a color image corresponding to the second section is displayed on the display module 23 as illustrated in FIG. 15C (A).

In the above-described example, illustrated have been the situations in which a single section of the second section is designated. However, the third embodiment is not limited to this, and it may be a situation in which a plurality of sections are designated as the second section, for example. For example, it may be a situation in which, within the first section "0.92-11.70 (sec)," two or more of the second sections are designated. In such a case, the system controller 21 defines a plurality of sections present within the first section as the second sections. The calculating module 261 then calculates the parameter values in the respective sections defined as the second sections. The generator 262 generates, based on the color information corresponding to the respective sections out of the color information corresponding to the feature quantity concerning the flow of the contrast material in the first section, and the feature quantity calculated in the respective sections, a plurality of color images corresponding to the respective sections.

While it may be a situation in which a plurality of sections are defined by designating the sections independent of each other within the first section, it may be a situation in which, by designating a single section within the first section, the designated section and other sections are defined as the second sections. For example, it may be a situation in which, when the second section "3.4-7.5 (sec)" is designated within the first section "0.92-11.70 (sec)," the system controller 21 defines the section "0.92-3.4 (sec)" and the section "7.5-11.70 (sec)" as the second sections. As in the foregoing, when a plurality of sections are defined as the second sections, the system controller 21 performs control such that color images corresponding to the respective sections are generated and displayed on the display module 23. For example, the system controller 21 displays the respective color images in the image display region R4, by switching each time the button 69 illustrated in FIG. 15A is depressed.

The generated color images may be displayed at the same time. FIG. 16 is a diagram illustrating a display example of a plurality of color images in the third embodiment. For example, as illustrated in FIG. 16, the system controller 21 displays, on the display module 23, a color image I7 corresponding to the section "0.92-3.4 (sec)" and a color image I8 corresponding to the section "7.5-11.70 (sec)," together with the color image I5 corresponding to the second section "3.4-7.5 (sec)." Consequently, as illustrated in FIG. 16, the X-ray diagnostic apparatus 100 in the third embodiment can display the color image I7 in which only arteries are represented, the color image I5 in which only capillaries are represented, and the color image I6 in which only veins are represented, without losing the correspondence relation of colors and blood vessels (for example, arteries are in red and veins are in blue), and thus enables the observer to perceive a state of each blood vessel easily. As a result, the X-ray diagnostic apparatus 100 in the third embodiment makes it possible to improve the diagnostic efficiency in parametric imaging.

While the situation in which three of the second sections are defined within the first section has been explained in the above-described example, the embodiment is not limited to this, and it may be a situation in which two of or four or more of the second sections are defined within the first section. Furthermore, it may be a situation of including overlapping sections when a plurality of second sections are defined within the first section. For example, it may be a situation in which the section "0.92-6.0 (sec)" and the section "5.3-11.70 (sec)" are defined within the first section "0.92-11.70 (sec)" as the second sections.

It may further be a situation in which a shorter section is defined within the second section that is defined within the first section. For example, it may be a situation in which the section "0.92-6.0 (sec)" is defined within the first section "0.92-11.70 (sec)" as the second section and the section "1.5-3.4 (sec)" is further defined within the section "0.92-6.0 (sec)."

In the above-described examples, explained have been the situations of improving the diagnostic efficiency of blood vessels by improving the rendering of images by parametric imaging. However, the third embodiment can be applied not only to the foregoing points but also to the image deterioration by the body movement of the subject. For example, when the subject moves while contrast-enhanced images are radiographed with time, the change in the signal intensity of each pixel in DSA images is to undergo not only the change by the contrast material but also the change by body movement, and thus the TDC of each pixel is not what the contrast material is reflected in. When the parametric imaging is performed by using such a TDC, displaying an accurate color image is very difficult.

Consequently, when the parametric imaging is performed by using the DSA images in which the body movement of the subject occurred at the time of radiographing, applying the method in the third embodiment makes it possible to perform the accurate parametric imaging from the X-ray images of up to immediately before the occurrence of the body movement. For example, the operator designates an image immediately before the occurrence of body movement while observing a moving image of DSA images in which the body movement of the subject has occurred at the time of radiographing to define the section just before the occurrence of body movement from the start of radiographing as the second section. The system controller 21 controls the calculating module 261 and the generator 262 so as to generate a color image corresponding to the defined second section. Consequently, a color image that has no influence of the body movement can be displayed.

In the foregoing embodiments, the situations in which the X-ray diagnostic apparatus performs various processing have been explained. However, it may be a situation in which the above-described processing is performed by an image processing apparatus such as a workstation. That is, it may be a situation in which the image processing apparatus includes the calculating module 261, the generator 262, and the system controller 21, and the various modules perform the above-described processing.

In the foregoing embodiments, explained has been the X-ray diagnostic apparatus provided with the C-arm as one example. However, the embodiment is not limited to this. For example, it may be an X-ray diagnostic apparatus in which an X-ray source and an X-ray detector are provided on different arms. In one example, as illustrated in FIG. 17, it may be a situation of using an X-ray diagnostic apparatus in which the X-ray detector 16 is supported by an arm 71 extending from the ceiling and the X-ray tube 12 is supported by an arm 72 extending from the floor. FIG. 17 is a diagram illustrating one example of the X-ray diagnostic apparatus in the third embodiment.

As in the foregoing, in accordance with the first to the third embodiments, the X-ray diagnostic apparatus and the image processing apparatus in the embodiments make it possible to improve the rendering of images by parametric imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to
calculate a feature quantity concerning a flow of a contrast material for each pixel in a first time period based on a temporal transition in signal intensity of the contrast material in the first time period of a plurality of X-ray images radiographed in time series by using the contrast material;
generate a color table in which the feature quantity and color are associated with each other;
generate a first color image, each pixel of the first color image having a color converted, by using the color table, from the feature quantity of each pixel in the first time period;
set a second time period that is within the first time period;
calculate the feature quantity concerning a flow of the contrast material for each pixel in the second time period based on a temporal transition in signal intensity of the contrast material in the second time period; and
generate a second color image, each pixel of the second color image having a color converted, by using the color table, from the feature quantity of the each pixel in the second time period.

2. The X-ray diagnostic apparatus according to claim 1, wherein the processing circuitry is further configured to
set a plurality of the second time periods within the first time period, and
generate a plurality of color images corresponding to the respective second time periods based on the color table.

3. The X-ray diagnostic apparatus according to claim 1, wherein the processing circuitry is further configured to
receive an operation of designating the second time period.

4. The X-ray diagnostic apparatus according to claim 3, wherein the processing circuitry is further configured to receive the operation of designating the second time period by a slide bar designating an end portion of the second time period along a time axis.

5. The X-ray diagnostic apparatus according to claim 3, wherein the processing circuitry is further configured to receive the operation of designating the second time period by a slide bar moving a time period of a predetermined width along a time axis.

6. The X-ray diagnostic apparatus according to claim 3, wherein the processing circuitry is further configured to receive the operation of designating the second time period by receiving a frame number or time of the X-ray images.

7. The X-ray diagnostic apparatus according to claim 3, wherein the processing circuitry is further configured to receive the operation of designating the second time period by the X-ray images displayed on a display.

8. The X-ray diagnostic apparatus according to claim 1, wherein the processing circuitry is further configured to calculate the feature quantity, which is information on time required until a peak of the signal intensity appears from a predetermined timing at which injection of the contrast material into a subject is started.

9. The X-ray diagnostic apparatus according to claim 1, wherein the processing circuitry is further configured to set a time period corresponding to a single increase and decrease in the signal intensity as the second time period out of a plurality of increases and decreases in the signal intensity in the transition in signal intensity of the contrast material, and
calculate the feature quantity for each pixel based on the increase and decrease in the signal intensity included in the set time period.

10. The X-ray diagnostic apparatus according to claim 9, wherein the processing circuitry is further configured to
determine a boundary of a plurality of increases and decreases in the signal intensity, by using the temporal transition in the signal intensity of the contrast material in a blood vessel region included in a plurality of X-ray images radiographed in time series by using the contrast material and the temporal transition in the signal intensity of the contrast material in a non-blood vessel region included in the X-ray images, and set a time period corresponding to a single increase and decrease as the second time period out of the increases and decreases based on the determined boundary.

11. The X-ray diagnostic apparatus according to claim 10, wherein the processing circuitry is further configured to determine a position of intersection as the boundary of a plurality of increases and decreases in the signal intensity when the temporal transition in the signal intensity of the contrast material in the blood vessel region and the temporal transition in the signal intensity of the contrast material in the non-blood vessel region are aligned in chronological order and are superimposed after maximum values of the respective signal intensities are normalized.

12. The X-ray diagnostic apparatus according to claim 10, wherein the processing circuitry is further configured to extract a region for which arrival time of the contrast material is early in the X-ray images as the blood vessel region, and extract a an region different from the extracted blood vessel region as the non-blood vessel region.

13. The X-ray diagnostic apparatus according to claim 10, wherein the processing circuitry is further configured to calculate a temporal transition in the signal intensity of the contrast material in high-frequency images included in the X-ray images as the temporal transition in the signal intensity of the contrast material in the blood vessel region.

14. The X-ray diagnostic apparatus according to claim 10, wherein the processing circuitry is further configured to calculate a temporal transition in the signal intensity of the contrast material in low-frequency images included in the X-ray images as the temporal transition in the signal intensity of the contrast material in the non-blood vessel region.

15. The X-ray diagnostic apparatus according to claim 10, wherein the processing circuitry is further configured to calculate the temporal transition in the signal intensity of the contrast material in a blood vessel region, based on a region of interest defined in the blood vessel region included in the X-ray images.

16. The X-ray diagnostic apparatus according to claim 10, wherein the processing circuitry is further configured to calculate the temporal transition in the signal intensity of the contrast material in the non-blood vessel region, based on a whole radiographed subject included in the X-ray images or on a region of interest of a predetermined size defined in the X-ray images.

17. The X-ray diagnostic apparatus according to claim 11, wherein the processing circuitry is further configured to
determine whether a maximum value of the signal intensity is of an end portion of the second time period for each pixel when calculating the feature quantity in the flow of the contrast material for each pixel based on the temporal transition in the signal intensity of the contrast material in the second time period,
generate information indicating that the pixel is of a singular value when the maximum value of the signal intensity is determined to be of the end portion of the second time period, and
cause the display to display the information indicative of the singular value.

18. The X-ray diagnostic apparatus according to claim 17, wherein the processing circuitry is further configured to
extract a peak in the second time period when the maximum value of the signal intensity is determined to be of the end portion of the second time period, and
calculate the feature quantity based on the extracted peak.

19. An X-ray diagnostic apparatus, comprising:
processing circuitry configured to
calculate a feature quantity concerning a flow of a contrast material for each pixel in a plurality of time periods based on a temporal transition in signal intensity of the contrast material in the plurality of time periods of a plurality of X-ray images radiographed in time series by using the contrast material, respectively;
generate a plurality of images in which the calculated feature quantity for each pixel is reflected in the pixel and corresponds to the plurality of time periods, respectively; and
cause a display to display the generated images.

20. An image processing apparatus, comprising:
processing circuitry configured to
calculate a feature quantity concerning a flow of a contrast material for each pixel in a first time period based on a temporal transition in signal intensity of the contrast material in the first time period of a plurality of X-ray images radiographed in time series by using the contrast material;
generate a color table in which the feature quantity and color are associated with each other;
generate a first color image, each pixel of the first color image having a color converted, by using the color table, from the feature quantity of each pixel in the first time period,
set a second time period that is within the first time period,
calculate the feature quantity concerning a flow of the contrast material for each pixel in the second time period based on a temporal transition in signal intensity of the contrast material in the second time period; and
generate a second color image, each pixel of the second color image having a color converted, by using the color table, from the feature quantity of the each pixel in the second time period.

* * * * *